(12) United States Patent
Celermajer et al.

(10) Patent No.: US 12,208,027 B2
(45) Date of Patent: Jan. 28, 2025

(54) COMBINATORIAL THERAPIES INCLUDING IMPLANTABLE DAMPING DEVICES AND THERAPEUTIC AGENTS FOR TREATING A CONDITION AND ASSOCIATED SYSTEMS AND METHODS OF USE

(71) Applicant: The Brain Protection Company PTY LTD, Paddington (AU)

(72) Inventors: David Stephen Celermajer, Vaucluse (AU); Anthony John Ujhazy, East Lindfield (AU); Zoran Milijasevic, Bayview (AU); Mark Carnegie, Sydney (AU)

(73) Assignee: The Brain Protection Company PTY LTD, Paddington (AU)

( * ) Notice: Subject to any disclaimer, the term of this patent is extended or adjusted under 35 U.S.C. 154(b) by 704 days.

(21) Appl. No.: 17/299,464

(22) PCT Filed: Nov. 26, 2019

(86) PCT No.: PCT/US2019/063309
§ 371 (c)(1),
(2) Date: Jun. 3, 2021

(87) PCT Pub. No.: WO2020/117562
PCT Pub. Date: Jun. 11, 2020

(65) Prior Publication Data
US 2022/0008229 A1 Jan. 13, 2022

Related U.S. Application Data

(60) Provisional application No. 62/775,107, filed on Dec. 4, 2018.

(51) Int. Cl.
*A61F 2/24* (2006.01)
*A61F 2/06* (2013.01)
(Continued)

(52) U.S. Cl.
CPC .................. *A61F 2/82* (2013.01); *A61F 2/06* (2013.01); *C07K 16/247* (2013.01);
(Continued)

(58) Field of Classification Search
CPC .. A61F 2/06; A61F 2/07; A61F 2/2418; A61F 2002/068; A61F 2/04;
(Continued)

(56) References Cited

U.S. PATENT DOCUMENTS

| 3,657,744 A | 4/1972 | Ersek |
| 3,726,279 A | 4/1973 | Barefoot |

(Continued)

FOREIGN PATENT DOCUMENTS

| DE | 102004018255 | 11/2005 |
| EP | 1442757 | 8/2004 |

(Continued)

OTHER PUBLICATIONS

Cifuentes et al., "Hypertension Accelerates the Progression of Alzheimer-Like Pathology in a Mouse Model of the Disease," hyper.ahajournals, Jun. 2015, 7 pgs.
(Continued)

*Primary Examiner* — Seema Mathew
(74) *Attorney, Agent, or Firm* — Perkins Coie LLP

(57) ABSTRACT

Devices, systems, and methods for combinatorial treatment of a condition with an implantable damping device and therapeutic agent (e.g., drug) are disclosed herein. Methods for treating one or more effects of the condition, such as a neurological condition, include providing the implantable damping device and at least one other therapy, such as a therapeutic agent, that treats the condition to the patient. The implantable damping device includes a flexible damping member and an abating substance and can be placed in apposition with a blood vessel. The flexible damping mem- (Continued)

ber forms a generally tubular structure having an inner and an outer surface, the inner surface formed of a sidewall having a partially deformable portion. The abating substance is disposed within the partially deformable portion and moves longitudinally and/or radially within the partially deformable portion in response to pulsatile blood flow.

15 Claims, 6 Drawing Sheets

(51) Int. Cl.
  *A61F 2/82* (2013.01)
  *C07K 16/24* (2006.01)
(52) U.S. Cl.
  CPC . *A61F 2002/068* (2013.01); *A61F 2220/0066* (2013.01); *A61F 2220/0075* (2013.01); *A61F 2230/0069* (2013.01); *A61F 2230/0091* (2013.01); *A61F 2250/0067* (2013.01); *C07K 2317/24* (2013.01)
(58) Field of Classification Search
  CPC .. A61F 2250/0003; A61F 2/2475; A61F 2/24; A61B 17/00; A61B 17/12109
  See application file for complete search history.

(56) References Cited

U.S. PATENT DOCUMENTS

| | | | |
|---|---|---|---|
| 4,881,939 A | 11/1989 | Newman | |
| 5,002,531 A | 3/1991 | Bonzel | |
| 5,100,429 A | 3/1992 | Sinofsky et al. | |
| 5,222,980 A | 6/1993 | Gealow | |
| 5,618,301 A | 4/1997 | Hauenstein | |
| 5,634,895 A | 6/1997 | Igo | |
| 5,665,117 A | 9/1997 | Rhodes | |
| 5,702,419 A | 12/1997 | Berry | |
| 5,755,777 A | 5/1998 | Chuter | |
| 5,800,524 A | 9/1998 | Borghi | |
| 5,800,526 A | 9/1998 | Anderson et al. | |
| 5,919,224 A | 7/1999 | Thompson et al. | |
| 6,010,529 A | 1/2000 | Herweck | |
| 6,030,336 A | 2/2000 | Franchi | |
| 6,042,605 A | 3/2000 | Martin et al. | |
| 6,120,534 A | 9/2000 | Ruiz | |
| 6,129,756 A | 10/2000 | Kugler et al. | |
| 6,149,681 A * | 11/2000 | Houser | A61F 2/966 |
| | | | 623/1.12 |
| 6,241,691 B1 | 6/2001 | Ferrera et al. | |
| 6,350,282 B1 | 2/2002 | Eberhardt | |
| 6,395,019 B2 | 5/2002 | Chobotov | |
| 6,974,473 B2 | 12/2005 | Barclay et al. | |
| 6,984,201 B2 | 1/2006 | Khaghani | |
| 7,125,464 B2 | 10/2006 | Chobotov et al. | |
| 7,147,661 B2 | 12/2006 | Chobotov | |
| 7,575,594 B2 | 8/2009 | Sieracki | |
| 7,766,814 B2 | 8/2010 | Walsh | |
| 7,819,941 B2 | 10/2010 | Kunze | |
| 8,702,776 B2 | 4/2014 | Heltai | |
| 8,708,906 B1 | 4/2014 | Orehek | |
| 8,876,850 B1 | 11/2014 | Vollmers | |
| 9,017,359 B2 | 4/2015 | Scandurra | |
| 9,039,725 B1 | 5/2015 | Vollmers | |
| 9,125,567 B2 | 9/2015 | Gross et al. | |
| 9,242,082 B2 | 1/2016 | Vollmers | |
| 9,492,293 B2 | 11/2016 | Richter et al. | |
| 9,592,068 B2 | 3/2017 | Janardhan et al. | |
| 10,064,626 B2 * | 9/2018 | Celermajer | A61B 17/12136 |
| 10,426,469 B2 * | 10/2019 | Shelton, IV | A61B 17/068 |
| 10,653,510 B2 * | 5/2020 | Fikfak | A61F 2/852 |
| 10,850,084 B1 * | 12/2020 | Rayhanabad | A61M 25/0032 |
| 10,973,527 B2 * | 4/2021 | Deshmukh | A61B 17/12172 |
| 11,224,433 B2 | 1/2022 | Celermajer et al. | |
| 2001/0027338 A1 | 10/2001 | Greenberg | |
| 2002/0188341 A1 | 12/2002 | Elliott | |
| 2003/0065303 A1 | 4/2003 | Wellman | |
| 2003/0125797 A1 | 7/2003 | Chobotov et al. | |
| 2004/0010303 A1 | 1/2004 | Bolea | |
| 2004/0106971 A1 | 6/2004 | Schwartz | |
| 2004/0143319 A1 | 7/2004 | Schwartz et al. | |
| 2004/0147803 A1 | 7/2004 | Hegde | |
| 2004/0260384 A1 | 12/2004 | Allen | |
| 2005/0021023 A1 | 1/2005 | Guglielmi et al. | |
| 2005/0049677 A1 | 3/2005 | Farnan | |
| 2005/0055082 A1 | 3/2005 | Muvhar | |
| 2006/0025852 A1 | 2/2006 | Armstrong et al. | |
| 2006/0047335 A1 * | 3/2006 | Israel | A61F 2/954 |
| | | | 623/1.11 |
| 2006/0052866 A1 | 3/2006 | Gilles et al. | |
| 2006/0100530 A1 | 5/2006 | Kliot et al. | |
| 2006/0106449 A1 | 5/2006 | Ben Muvhar | |
| 2006/0155366 A1 * | 7/2006 | LaDuca | A61F 2/954 |
| | | | 606/108 |
| 2006/0259128 A1 * | 11/2006 | Pavcnik | A61F 2/2427 |
| | | | 623/1.24 |
| 2007/0156167 A1 | 7/2007 | Connors et al. | |
| 2008/0109087 A1 * | 5/2008 | Durgin | A61F 5/0079 |
| | | | 623/23.65 |
| 2008/0140110 A1 * | 6/2008 | Spence | A61F 2/06 |
| | | | 623/1.1 |
| 2008/0194905 A1 | 8/2008 | Walsh | |
| 2009/0177279 A1 | 7/2009 | Luciano et al. | |
| 2010/0030253 A1 | 2/2010 | Harris et al. | |
| 2010/0056978 A1 | 3/2010 | Machan et al. | |
| 2010/0057192 A1 * | 3/2010 | Celermajer | A61B 17/11 |
| | | | 623/1.26 |
| 2010/0070019 A1 * | 3/2010 | Shalev | A61F 2/06 |
| | | | 623/1.46 |
| 2010/0256735 A1 | 10/2010 | Morales, Jr. | |
| 2011/0106240 A1 | 5/2011 | Chuter | |
| 2011/0144669 A1 | 6/2011 | Becking et al. | |
| 2011/0166240 A1 | 7/2011 | Chuter | |
| 2011/0196967 A1 | 8/2011 | Tachibana | |
| 2011/0213408 A1 | 9/2011 | Gross et al. | |
| 2011/0257725 A1 * | 10/2011 | Argentine | A61F 2/07 |
| | | | 623/1.15 |
| 2012/0089218 A1 | 4/2012 | Dardi | |
| 2013/0013051 A1 | 1/2013 | Benary | |
| 2013/0066416 A1 | 3/2013 | Goicoechea et al. | |
| 2013/0079871 A1 | 3/2013 | Scandurra et al. | |
| 2013/0172981 A1 | 7/2013 | Gross | |
| 2013/0218191 A1 | 8/2013 | Heltai | |
| 2013/0226280 A1 * | 8/2013 | O'Rourke | A61F 2/06 |
| | | | 623/1.35 |
| 2013/0274648 A1 * | 10/2013 | Weinberger | A61M 1/3655 |
| | | | 604/9 |
| 2013/0296917 A1 | 11/2013 | Rees | |
| 2014/0058436 A1 * | 2/2014 | Rosenbluth | A61B 17/12172 |
| | | | 606/200 |
| 2014/0088692 A1 * | 3/2014 | Wright | A61F 2/2436 |
| | | | 623/2.11 |
| 2014/0200504 A1 * | 7/2014 | Rocha-Singh | A61N 5/062 |
| | | | 604/509 |
| 2014/0343664 A1 * | 11/2014 | Furey | A61B 17/12145 |
| | | | 623/1.18 |
| 2014/0350658 A1 | 11/2014 | Benary | |
| 2015/0025625 A1 | 1/2015 | Rylski et al. | |
| 2015/0088239 A1 | 3/2015 | Ben-Muvhar | |
| 2015/0359631 A1 * | 12/2015 | Sheahan | A61F 2/2418 |
| | | | 623/2.19 |
| 2016/0113764 A1 * | 4/2016 | Sheahan | A61F 2/2418 |
| | | | 623/2.17 |
| 2016/0324898 A1 * | 11/2016 | Bolmont | A61K 38/28 |
| 2017/0042551 A1 * | 2/2017 | Celermajer | A61B 17/12136 |
| 2017/0049588 A1 * | 2/2017 | Davis | A61F 2/856 |
| 2017/0087045 A1 | 3/2017 | Zhadkevich | |
| 2017/0172771 A1 | 6/2017 | Bruckheimer et al. | |
| 2017/0173262 A1 | 6/2017 | Veltz | |
| 2017/0252144 A1 * | 9/2017 | Hannon | A61L 27/025 |
| 2017/0333184 A1 * | 11/2017 | Ryan | A61F 2/2433 |
| 2018/0008279 A1 * | 1/2018 | Celermajer | A61B 17/12136 |

(56) References Cited

U.S. PATENT DOCUMENTS

| | | | |
|---|---|---|---|
| 2018/0214157 A1 | 8/2018 | Celermajer et al. | |
| 2018/0235745 A1* | 8/2018 | Seybold | A61B 34/10 |
| 2019/0069903 A1* | 3/2019 | Deshmukh | A61B 17/1204 |
| 2019/0336133 A1 | 7/2019 | Celermajer et al. | |
| 2019/0254814 A1* | 8/2019 | Nitzan | A61F 2/2412 |
| 2019/0307459 A1* | 10/2019 | Celermajer | A61M 60/161 |
| 2019/0374213 A1* | 12/2019 | Goldsmith | A61M 27/008 |
| 2020/0375721 A1 | 12/2020 | Celermajer et al. | |
| 2021/0007839 A1 | 1/2021 | Du | |
| 2021/0085935 A1* | 3/2021 | Fahey | A61B 17/11 |
| 2021/0186723 A1* | 6/2021 | Coyne | A61F 2/2412 |
| 2021/0393189 A1 | 12/2021 | Celermajer et al. | |
| 2022/0022881 A1 | 1/2022 | Celermajer et al. | |
| 2022/0039804 A1* | 2/2022 | Rangwala | A61B 17/12172 |
| 2022/0233200 A1 | 7/2022 | Celermajer et al. | |
| 2022/0401683 A1* | 12/2022 | Namon | A61F 5/08 |
| 2023/0000620 A1* | 1/2023 | Ryan | A61F 2/2436 |
| 2023/0059358 A1* | 2/2023 | Tillman | A61M 25/1011 |
| 2023/0172610 A1* | 6/2023 | Celermajer | C12Y 207/11013 604/508 |
| 2023/0293283 A1* | 9/2023 | Takahashi | A61F 2/06 623/1.39 |
| 2023/0363885 A1* | 11/2023 | Hannon | A61F 2/04 |
| 2023/0381546 A1* | 11/2023 | Yu | A61N 7/00 |

FOREIGN PATENT DOCUMENTS

| | | |
|---|---|---|
| EP | 1600123 | 11/2005 |
| EP | 2586402 | 5/2013 |
| JP | 5782523 | 2/2014 |
| WO | WO1996032077 | 10/1996 |
| WO | WO2001056501 | 8/2001 |
| WO | WO2003028522 | 4/2003 |
| WO | WO2004026112 | 4/2004 |
| WO | WO2004056274 | 7/2004 |
| WO | WO2005041783 | 5/2005 |
| WO | WO2005084730 | 9/2005 |
| WO | WO2006062976 | 6/2006 |
| WO | WO2007038476 | 4/2007 |
| WO | WO2008061185 | 5/2008 |
| WO | WO2012018590 | 2/2012 |
| WO | WO2012071395 | 5/2012 |
| WO | WO2013013081 | 1/2013 |
| WO | WO2013084235 | 6/2013 |
| WO | WO2014127042 | 8/2014 |
| WO | WO2014186755 | 11/2014 |
| WO | WO2004106971 | 12/2014 |
| WO | WO2016128983 | 8/2016 |
| WO | WO2017024357 | 2/2017 |
| WO | WO2017141246 | 8/2017 |
| WO | WO2018027298 | 2/2018 |
| WO | WO2018064769 | 4/2018 |
| WO | WO2018102824 | 6/2018 |
| WO | WO2018146184 | 8/2018 |
| WO | WO2020073094 | 4/2020 |
| WO | WO2020117560 | 6/2020 |
| WO | WO2020117562 | 6/2020 |

OTHER PUBLICATIONS

Cullen, et al. "Microvascular pathology in the aging human brain: Evidence that senile plaques are sites of microhaemorrhages." Neurobiology of Aging (2006) 27, Jan. 2006, pp. 1786-1796.

Ding et al., "Carotid Arterial Stiffness and Risk of Incident Cerebral Microbleeds in Older People," Arterioscler Thromb Vasc Biol, Jun. 11, 2015, 7 pgs.

Messas et al. "Arterial wall elasticity: State of the art and future prospects," Diagnostic and Interventional Imaging, (2013) 94, http://dx.doi.org/10.1016/j.diii., Jan. 2013, pp. 561-569.

Mitchell et al. "Arterial Stiffness, pressure and flow pulsatility and brain structure and function: the Age, Gene/Environment Susceptibility—Reykjavik Study," Brain (2011) 134; received Aug. 2011, 3398-3407.

Stone et al. "The Mechanical Cause of Age-Related Dementia (Alzheimer's Disease): The Brain is Destroyed by the Pulse," Journal of Alzheimer's Disease (2015) 44; accepted Sep. 2014, pp. 355-373.

International Preliminary Report on Patentability issued for International Application No. PCT/AU2016/050734, Applicant: The Brain Protection Company Pty Ltd, Date of Mailing: Jan. 2, 2018, 55 pages.

Takaiwa A. et al., "Changes in cognitive function during the 1-year period following endarterectomy and stenting of patients with high-grade carotid artery stenosis," Acta Neurochir, 2009, Published online Jun. 2009, vol. 151, pp. 1593-1600.

Grunwald I. Q. et al., "Influence of carotid artery stenting on cognitive function," Neuroradiology, 2010, Published online Nov. 2009, vol. 52, pp. 61-66.

Raabe R.D. et al., "One-year Cognitive Outcomes Associated with Carotid Artery Stent Placement," J Vasc Interv Radiol, 2010, vol. 21, DOI: 10.1016/j.jvir., Mar. 2010, pp. 983-988.

Lal B. K. et al., "Cognitive changes after surgery vs stenting for carotid artery stenosis," J Vasc Surg, 2011, Mar. 2011, vol. 54, pp. 691-698.

Chen Y-H et al., "Carotid stenting improves cognitive function in asymptomatic cerebral ischemia," International Journal of Cardiology, 2012, Received Jul. 2011, vol. 157, pp. 104-107.

Richard E. et al., "Prevention of dementia by intensive vascular care (preDIVA); a cluster-randomised trial in progress," Chapter 4.1 Alzheimer disease and associated disorders, Jul. 2009, pp. 46 to 58.

Dickstein D. L. et al., "Role of Vascular Risk Factors and Vascular Dysfunction in Alzheimer's Disease," Mount Sinai Journal of Medicine, 2010, Published Jan.-Feb. 2010, vol. 77, pp. 82-102.

Power M.C. et al., "The association between blood pressure and incident Alzheimer disease: a systematic review and meta-analysis," Epidemiology, 2011, Sep. 2011, vol. 22(5), pp. 646-659.

European Search Report received for co-pending European Patent Application No. 16834323.4, Date of Mailing: Apr. 16, 2019, Applicant: The Brain Protection Company PTY Ltd, 10 pages.

English Translation of First Office Action received for co-pending Chinese Patent Application No. 201680048180.8, Date of Mailing: May 13, 2019, Applicant: The Brain Protection Company PTY Ltd, 3 pages.

Examination Report received for co-pending Australian Patent Application No. 2016306711, Date of Mailing: Feb. 7, 2019, Applicant: The Brain Protection Company PTY Ltd, 4 pages.

International Search Report and Written Opinion issued for International Application No. PCT/US19/63294, Applicant: The Brain Protection Company Pty Ltd, Date of Mailing: Apr. 24, 2020, 17 pages.

International Search Report and Written Opinion issued for International Application No. PCT/US19/63309, Applicant: The Brain Protection Company Pty Ltd, Date of Mailing: Apr. 21, 2020, 12 pages.

International Preliminary Report on Patentability received for International PCT Application No. PCT/AU2018/051191 filed Nov. 2, 2018; Applicant: The Brain Protection Company Pty Ltd; Date of Mailing: Feb. 10, 2020, 20 pages.

International Search Report and Written Opinion received for International PCT Application No. PCT/AU2018/051191 filed Nov. 2, 2018; Applicant: The Brain Protection Company Pty Ltd; Date of Mailing: Jan. 18, 2019, 20 pages.

International Search Report and Written Opinion received for International PCT Application No. PCT/AU2019/051101, filed Oct. 11, 2019; Applicant: The Brain Protection Company Pty Ltd; Date of Mailing: Dec. 19, 2019, 16 pages.

Sun et al., "Post-stroke cognitive impairment: epidemiology, mechanisms and management," Annals of Translational Medicine, 2014;2(8):80, published on Jul. 18, 2014, 16 pages.

International Preliminary Report on Patentability received for International PCT Application No. PCT/AU2020/051377, filed Dec. 16, 2020; Applicant: The Brain Protection Company Pty Ltd; Date of Mailing: Mar. 29, 2022, 20 pages.

European Search Report received for co-pending European Patent Application No. 16834323.4, Date of Mailing: Oct. 10, 2022, Applicant: The Brain Protection Company PTY Ltd, 5 pages.

(56) References Cited

OTHER PUBLICATIONS

Extended European Search Report received for co-pending European Patent Application No. 19891935.9, Date of Mailing: Dec. 13, 2022, Applicant: The Brain Protection Company PTY Ltd, 13 pages.

Sevigny et al., "The antibody aducanumab reduces Aβ plaques in Alzheimer's disease," Nature 537, 50-56 (2016), published on Aug. 31, 2016, 21 pages.

Panza et al., "Emerging drugs to reduce abnormal ß-amyloid protein in Alzheimer's disease patients," Expert Opinion on Emerging Drugs, vol. 21, No. 4, published on Oct. 6, 2016, 16 pages.

\* cited by examiner

COMBINATORIAL THERAPIES INCLUDING IMPLANTABLE DAMPING DEVICES AND THERAPEUTIC AGENTS FOR TREATING A CONDITION AND ASSOCIATED SYSTEMS AND METHODS OF USE

CROSS-REFERENCE TO RELATED APPLICATION

This application is a 35 U.S.C. § 371 U.S. National Phase application of International Patent Application No. PCT/US2019/063309, filed Nov. 26, 2019, and titled "COMBINATORIAL THERAPIES INCLUDING IMPLANTABLE DAMPING DEVICES AND THERAPEUTIC AGENTS FOR TREATING A CONDITION AND ASSOCIATED SYSTEMS AND METHODS OF USE," which claims the benefit of U.S. Patent Application No. 62/775,107, filed Dec. 4, 2018, and titled "COMBINATORIAL THERAPIES INCLUDING IMPLANTABLE DAMPING DEVICES AND THERAPEUTIC AGENTS FOR TREATING A CONDITION AND ASSOCIATED SYSTEMS AND METHODS OF USE," each of the above applications are incorporated herein by reference in their entireties.

TECHNICAL FIELD

The present technology relates to combinatorial therapies including an implantable damping device and therapeutic agents for treating a condition (e.g., a neurodegenerative condition such as dementia) and associated systems and methods of use. In particular, the present technology is directed to combinatorial therapies including an implantable damping device for positioning at, near, within, around, or in place of at least a portion of an artery and one or more therapeutic agents (e.g., drugs) for treating the condition.

BACKGROUND

The heart supplies oxygenated blood to the body through a network of interconnected, branching arteries starting with the largest artery in the body—the aorta. As shown in the schematic view of the heart and selected arteries in FIG. 1A, the portion of the aorta closest to the heart is divided into three regions: the ascending aorta (where the aorta initially leaves the heart and extends in a superior direction), the aortic arch, and the descending aorta (where the aorta extends in an inferior direction). Three major arteries branch from the aorta along the aortic arch: the brachiocephalic artery, the left common carotid artery, and the left subclavian artery. The brachiocephalic artery extends away from the aortic arch and subsequently divides into the right common carotid artery, which supplies oxygenated blood to the head and neck, and the right subclavian artery, which predominantly supplies blood to the right arm. The left common carotid artery extends away from the aortic arch and supplies the head and neck. The left subclavian artery extends away from the aortic arch and predominantly supplies blood to the left arm. Each of the right common carotid artery and the left common carotid artery subsequently branches into separate internal and external carotid arteries.

During the systole stage of a heartbeat, contraction of the left ventricle forces blood into the ascending aorta that increases the pressure within the arteries (known as systolic blood pressure). The volume of blood ejected from the left ventricle creates a pressure wave—known as a pulse wave—that propagates through the arteries propelling the blood. The pulse wave causes the arteries to dilate, as shown schematically in FIG. 1B. When the left ventricle relaxes (the diastole stage of a heartbeat), the pressure within the arterial system decreases (known as diastolic blood pressure), which allows the arteries to contract.

The difference between the systolic blood pressure and the diastolic blood pressure is the "pulse pressure," which generally is determined by the magnitude of the contraction force generated by the heart, the heart rate, the peripheral vascular resistance, and diastolic "run-off" (e.g., the blood flowing down the pressure gradient from the arteries to the veins), amongst other factors. High flow organs, such as the brain, are particularly sensitive to excessive pressure and flow pulsatility. To ensure a relatively consistent flow rate to such sensitive organs, the walls of the arterial vessels expand and contract in response to the pressure wave to absorb some of the pulse wave energy. As the vasculature ages, however, the arterial walls lose elasticity, which causes an increase in pulse wave speed and wave reflection through the arterial vasculature. Arterial stiffening impairs the ability of the carotid arteries and other large arteries to expand and dampen flow pulsatility, which results in an increase in systolic pressure and pulse pressure. Accordingly, as the arterial walls stiffen over time, the arteries transmit excessive force into the distal branches of the arterial vasculature.

Research suggests that consistently high systolic pressure, pulse pressure, and/or change in pressure over time (dP/dt) increases the risk of dementia, such as vascular dementia (e.g., an impaired supply of blood to the brain or bleeding within the brain). Without being bound by theory, it is believed that high pulse pressure can be the root cause or an exacerbating factor of vascular dementia and age-related dementia (e.g., Alzheimer's disease). As such, the progression of vascular dementia and age-related dementia (e.g., Alzheimer's disease) may also be affected by the loss of elasticity in the arterial walls and the resulting stress on the cerebral vessels. Alzheimer's Disease, for example, is generally associated with the presence of neuritic plaques and tangles in the brain. Recent studies suggest that increased pulse pressure, increased systolic pressure, and/or an increase in the rate of change of pressure (dP/dt) may, over time, cause microbleeds within the brain that may contribute to the neuritic plaques and tangles.

By 2050, it is estimated that at least one in every 85 people will be living with Alzheimer's disease world-wide and more than eight times as many people have shown preclinical symptoms. Additional disease-modifying therapies that will prevent or delay the onset or slow progression of neurological conditions, such as dementia, have been and are being developed. As of January 2018, there were 112 therapeutic agents undergoing clinical trials and/or other related testing for treatment of Alzheimer's disease, one of several neurological conditions that is becoming increasingly more common as the world's population ages. While these therapeutic agents may improve memory, behavior, cognition and/or reduce neuropsychiatric symptoms of Alzheimer's disease, additional studies testing the efficacy, safety, and tolerability of these therapeutic agents, and/or additional therapeutic agents are needed. Accordingly, there is a need for improved devices, systems, and methods for treating vascular and/or age-related dementia.

BRIEF DESCRIPTION OF THE DRAWINGS

Many aspects of the present disclosure can be better understood with reference to the following drawings. The components in the drawings are not necessarily to scale.

Instead, emphasis is placed on illustrating clearly the principles of the present disclosure.

DETAILED DESCRIPTION

Figure 1A:
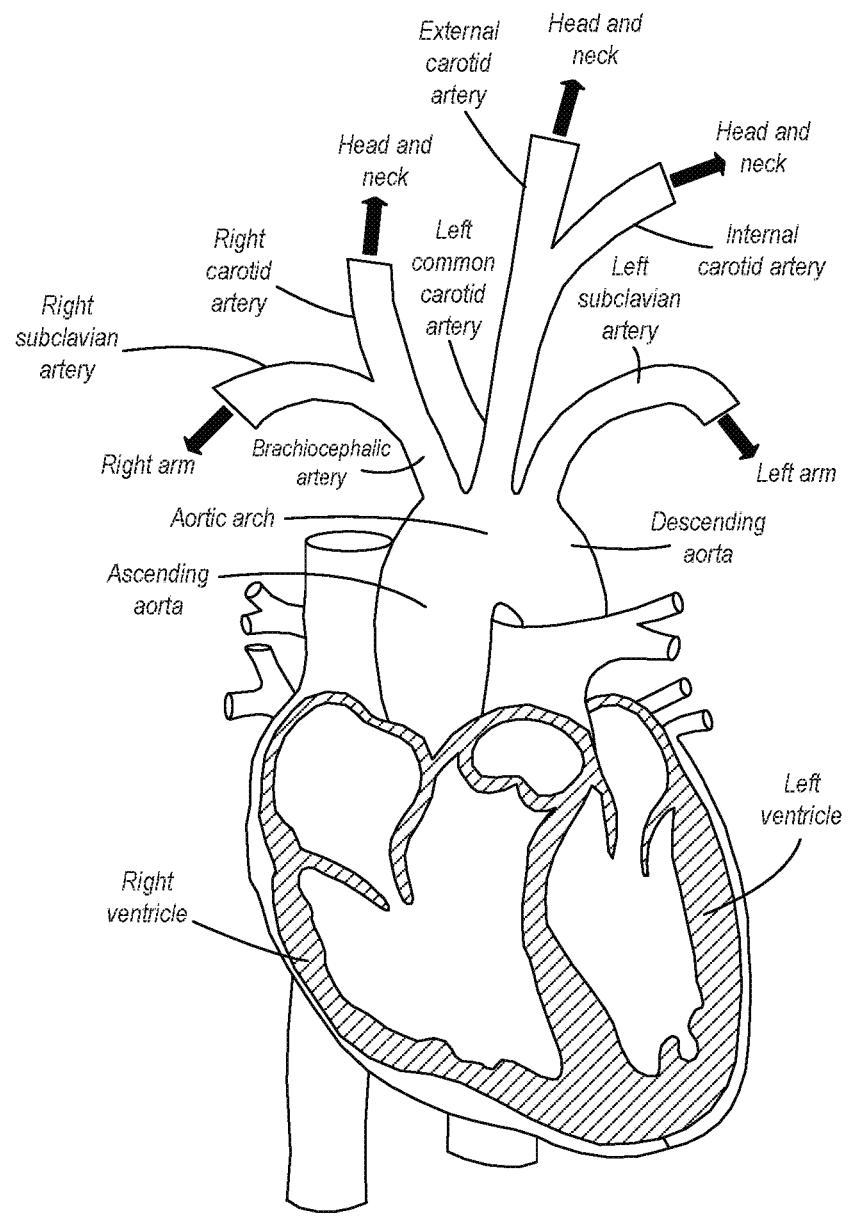
FIG. 1A is a schematic illustration of a human heart and a portion of the arterial system near the heart.
Figure 1B:
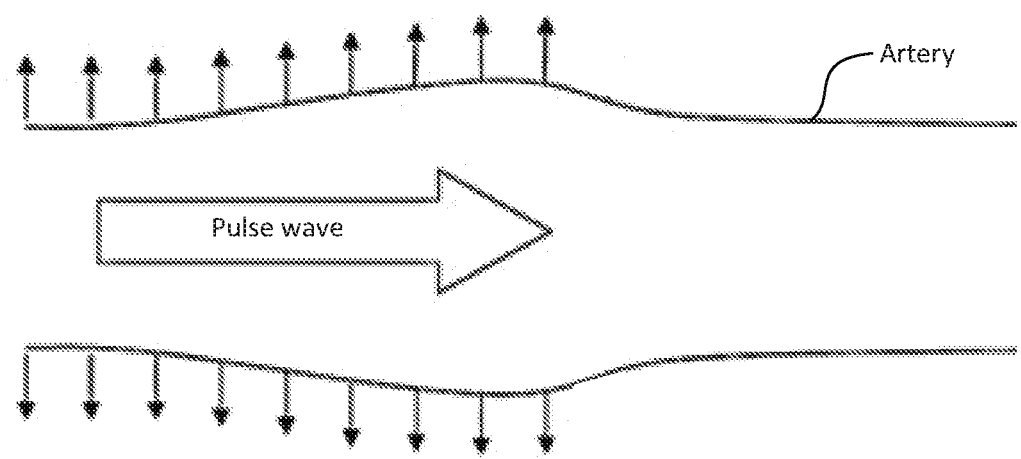
FIG. 1B is a schematic illustration of a pulse wave propagating along a blood vessel.

The present technology is directed to combinatorial therapies including an implantable damping device and a therapeutic agent (e.g., a drug) for treating or slowing the progression of a condition, including neurological conditions such as dementia (e.g., vascular dementia and age-related dementia), and associated systems and methods of use. Some embodiments of the present technology, for example, are directed to combinatorial device and drug therapies including damping devices having an anchoring member and a flexible, compliant damping member having an outer surface and an inner surface defining a lumen configured to direct blood flow. The inner surface is configured such that a cross-sectional dimension of the lumen varies. For example, the outer surface and the inner surface can be separated from each other by a distance that varies along the length of the damping member. The damping member can further include a first end portion, a second end portion opposite the first end portion, and a damping region between the first and second end portions. The distance between the outer surface and the inner surface of the damping member can be greater at the damping region than at either of the first or second end portions. When blood flows through the damping member during systole, the damping member absorbs a portion of the pulsatile energy of the blood to reduce the magnitude of the pulse pressure transmitted to a portion of the blood vessel distal to the damping device. Additional embodiments of the present technology, for example, are directed to combinatorial device and drug therapies including therapeutic agents (e.g., drugs) that have been developed or are currently being developed to treat or otherwise slow the effects of neurological conditions. These therapeutic agents, and other therapeutic agents derived from and/or otherwise based upon these therapeutic agents, are included in embodiments of the present technology. Specific details of several embodiments of the technology are described below with reference to FIGS. 1A-5.

With regard to the terms "distal" and "proximal" within this description, unless otherwise specified, the terms can reference a relative position of the portions of a damping device and/or an associated delivery device with reference to an operator, direction of blood flow through a vessel, and/or a location in the vasculature. For example, in referring to a delivery catheter suitable to deliver and position various damping devices described herein, "proximal" refers to a position closer to the operator of the device or an incision into the vasculature, and "distal" refers to a position that is more distant from the operator of the device or further from the incision along the vasculature (e.g., the end of the catheter).

As used herein, "artery" and "arteries that supply blood to the brain," include any arterial blood vessel (or portion thereof) that provides oxygenated blood to the brain. For example, "arteries" or "arteries that supply blood to the brain" can include the ascending aorta, the aortic arch, the brachiocephalic trunk, the right common carotid artery, the left common carotid artery, the left and right internal carotid arteries, the left and right external carotid arteries, and/or any branch and/or extension of any of the arterial vessels described above.

With regard to the term "neurological condition" within this description, unless otherwise specified, the term refers to a condition, a disorder, and/or a disease of the brain, spine, and nerves connecting the brain and the spine. Neurological conditions include, but are not limited to dementia (e.g., vascular, frontotemporal, Lewy body), Alzheimer's disease, Huntington's disease, cognitive impairment, Parkinson's disease, neuralgia, tumor, cancer, stroke, aneurysm, epilepsy, headache, and/or migraine.

The term "treatment" in relation a given condition, disease, or disorder includes, but is not limited to, inhibiting the disease or disorder, for example, arresting the development of the condition, disease, or disorder; relieving the condition, disease, or disorder, for example, causing regression of the condition, disease, or disorder; or relieving a condition caused by or resulting from the disease or disorder, for example, relieving, preventing or treating symptoms of the disease or disorder.

The term "prevention" in relation to a given condition, disease, or disorder means: preventing the onset of its development if none had occurred; preventing the condition, disease, or disorder from occurring in a subject that may be predisposed to the condition, disease, or disorder but has not yet been diagnosed as having the condition, disease; or disorder, and/or preventing further development of the condition, disease, or disorder if already present.

As used herein, "route" in relation to administration of one or more therapies, such as a therapeutic agent (e.g., drug), refers to a path by which the therapeutic agent is delivered to a subject, for example, a subject's body. A route of therapeutic administration include enteral and parenteral routes of administration. Enteral administration includes oral, rectal, intestinal, and/or enema. Parenteral includes topical, transdermal, epidural, intracerebral, intracerebroventricular, epicutaneous, sublingual, sublabial, buccal, inhalational (e.g., nasal), intravenous, intraarticular, intracardiac, intradermal, intramuscular, intraocular, intraosseous infusion, intraperitoneal, intrathecal, intravitreal, subcutaneous, perivascular, implantation, vaginal, otic, and/or transmucosal.

The use of numerical values in the various quantitative values specified in this application, unless expressly indicated otherwise, are stated as approximations as though the minimum and maximum values within the stated ranges were both preceded by the word "about." In this manner, slight variations from a stated value can be used to achieve substantially the same results as the stated value. Also, the disclosure of ranges is intended as a continuous range including every value between the minimum and maximum values recited, as well as any ranges that can be formed by such values. Also disclosed herein are any and all ratios (and ranges of any such ratios) that can be formed by dividing a recited numeric value into any other recited numeric value. Accordingly, the skilled person will appreciate that many such ratios, ranges, and ranges of ratios can be unambiguously derived from the numerical values presented herein; and, in all instances, such ratios, ranges, and ranges of ratios represent various embodiments of the present invention. Unless otherwise stated, the term "about" refers to values within 10% of a stated value.

While the present invention is capable of being embodied in various forms, the description below of several embodiments is made with the understanding that the present disclosure is to be considered as an exemplification of the invention and is not intended to limit the invention to the specific embodiments illustrated. Headings are provided for convenience only and are not to be construed to limit the invention in any manner. Embodiments illustrated under any heading may be combined with embodiments illustrated under any other heading.

I. SELECTED INTRAVASCULAR EMBODIMENTS OF DAMPING DEVICES

Figure 2A:
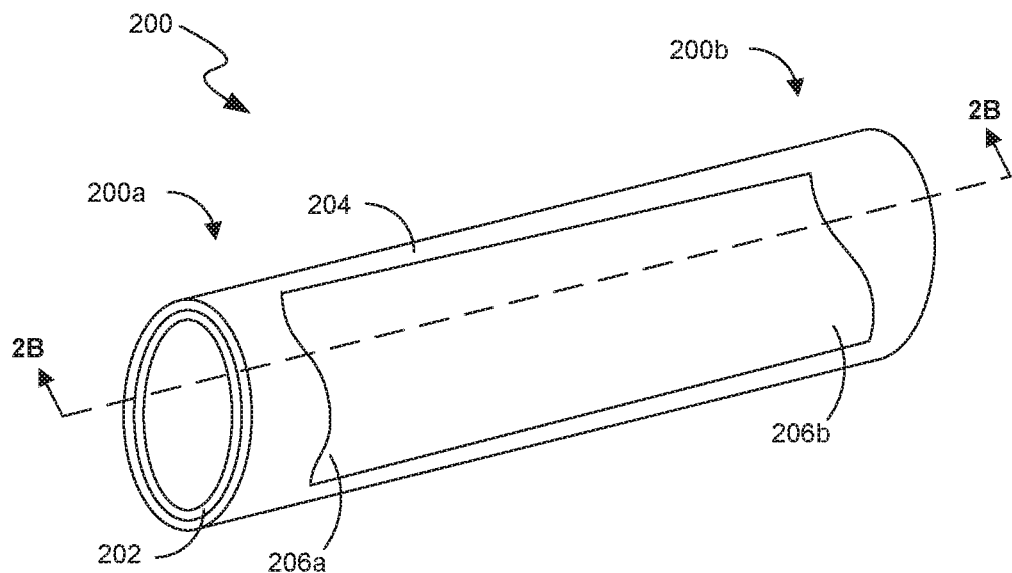
FIG. 2A is a perspective view of another embodiment of a damping device in accordance with the present technology.
Figure 2B:
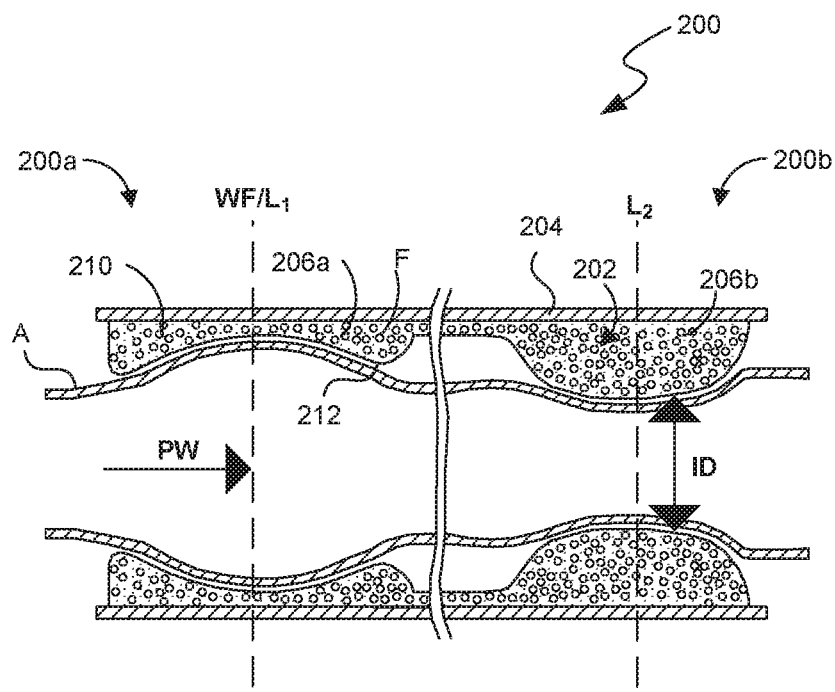
FIG. 2B is a cross-sectional view of the damping device shown in FIG. 2A, taken along line 2B-2B.

FIG. 2A is a perspective, cut-away view of a damping device 200 in accordance with the present technology in a deployed, relaxed state. FIG. 2B is a cross-sectional view of the damping device 200 positioned in an artery A during transmission of a pulse wave PW through the portion of the artery A surrounded by the damping device 200. Referring to FIGS. 2A and 2B together, the damping device 200 includes a damping member 202 and a structural member 204 coupled to the damping member 202. The damping member 202 may be a flexible, visoelastic damping member (e.g., a cushioning member). As shown in FIG. 2A, the damping device 200 can have a generally cylindrical shape in the deployed, relaxed state. The damping device 200 may be configured to wrap around the circumference of the artery with opposing longitudinal edges (not shown) secured to one another via sutures, staples, adhesive, and/or other suitable coupling devices. Alternatively, the damping device 200 can have a longitudinal slit for receiving the artery therethrough. In either of the foregoing extravascular embodiments, the damping device 200 is configured to be positioned around the circumference of the artery A so that the inner surface 212 (FIG. 2B) is adjacent and/or in contact with the outer surface of the arterial wall. In other embodiments, the damping device 200 can be configured to be positioned intravascularly (e.g., within the artery lumen) such that an outer surface of the damping device 200 is adjacent and/or in contact with the inner surface of the arterial wall. In such intravascular embodiments, the inner surface 212 of the damping member 202 is adjacent or directly in contact with blood flowing through the artery A.

The structural member 204 can be a generally cylindrical structure configured to expand from a low-profile state to a deployed state. The structural member 204 is configured to provide structural support to secure the damping device 200 to a selected region of the artery. In some embodiments, the structural member 204 can be a stent formed from a laser cut metal, such as a superelastic and/or shape memory material (e.g., Nitinol) or stainless steel. All or a portion of the structural member 204 can include a radiopaque coating to improve visualization of the device 200 during delivery, and/or the structural member 204 may include one or more radiopaque markers. In other embodiments, the structural member 204 may comprise a mesh or woven (e.g., a braid) construction in addition to or in place of a laser cut stent. For example, the structural member 204 can include a tube or braided mesh formed from a plurality of flexible wires or filaments arranged in a diamond pattern or other configuration. In some embodiments, all or a portion of the structural member 204 can be covered by a graft material (such as Dacron) to promote sealing with the vessel wall. Additionally, all or a portion of the structural member 204 can include one or more biomaterials.

In the embodiment shown in FIGS. 2A and 2B, the structural member 204 is positioned radially outwardly of the damping member 202 and extends along the entire length of the damping member 202 (though a middle portion of the structural member 204 is cut-away in FIG. 2A for illustrative purposes only). In other embodiments, the structural member 204 and the damping member 202 may have other suitable configurations. For example, the damping device 200 can include more than one structural member 204 (e.g., two structural members, three structural members, etc.). Additionally, in some embodiments the structural member(s) 204 may extend along only a portion of the damping member 202 such that a portion of the length of the damping member 202 is not surrounded and/or axially aligned with any portion of the structural member 204. Also, in some embodiments, all or a portion of the damping member 202 may be positioned radially outwardly of all or a portion of the structural member 204.

In the embodiment shown in FIGS. 2A and 2B, the damping member 202 includes a proximal damping element 206a and a distal damping element 206b. The damping member 202 may further include optional channels (not shown) extending between the proximal and distal damping elements 206a, 206b. The channels, for example, can extend in a longitudinal direction along the damping device 200 and fluidly couple the proximal damping element 206a to the distal damping element 206b. The damping member 202 may further include an abating substance 210 (FIG. 2B) configured to deform in response to fluid stress (such as blood flow), thereby absorbing at least a portion of the stress. For example, as best shown in FIG. 2B, in one embodiment the abating substance 210 includes a plurality of fluid particles F (only one fluid particle labeled) contained in the proximal damping element 206a, distal damping element 206b, and channel(s) 208. As used herein, the term "fluid" refers to liquids and/or gases, and "fluid particles" refers to liquid particles and/or gas particles. In some embodiments, the damping member 202 is a gel, and the plurality of fluid particles F are dispersed within a network of solid particles. In other embodiments, the damping member 202 may include only fluid particles F (e.g., only gas particles, only liquid particles, or only gas and liquid particles) contained within a flexible and/or elastic membrane that defines the proximal damping member 206a, the distal damping member 206b, and the channel(s) 208. The viscosity and/or composition of the abating substance 210 may be the same or may vary along the length and/or circumference of the damping member 202.

Referring to FIG. 2B, when a pulse wave PW traveling through the artery A applies a stress at a first axial location L1 along the length of the damping member 202 (e.g., at wavefront WF), at least a portion of the fluid particles move away from the first axial location L1 to a second axial location L2 along the length of the damping member 202. As such, at least a portion of the fluid particles are redistributed along the length of the damping member 202 such that the inner diameter ID of the damping member 202 increases at the first axial location L1 while the inner diameter ID decreases at another axial location (e.g., L2). For example, as the wavefront WF passes through the proximal portion 200a of the device 200, the portion of the artery A aligned with the wavefront WF dilates, thereby applying a stress to the proximal damping element 206a and forcing at least some of the fluid particles in the proximal damping element 206a to move distally within the damping member 202. At least some of the displaced fluid particles are forced into the distal damping element 206b, thereby increasing the volume of the distal damping element 206b and decreasing the inner diameter ID of the damping device 200 at the distal portion 200b. The decreased inner diameter ID of the damping device 200 provides an impedance to the blood flow that absorbs at least a portion of the energy in the pulse wave when the blood flow reaches the distal damping member 206b. As the wavefront WF then passes through the distal portion 200b of the device 200, the portion of the artery A aligned with the wavefront WF dilates, thereby applying a stress to the distal damping element 206b and forcing at least some of the fluid particles currently in the distal damping element 206b to move proximally within the damping member 202. At least some of the displaced fluid particles are forced into the proximal damping element 206a, thereby increasing the volume of the proximal damping element 206a and decreasing the inner diameter ID of the device 200 at the proximal portion 200a. Movement of the fluid particles and/or deformation of the damping member 202 in response to the pulse wave absorbs at least a portion of the energy carried by the pulse wave, thereby reducing the stress on the arterial wall distal to the device.

When the damping member 202 deforms in response to the pulse wave, the shape of the structural member 204 may remain generally unchanged, thereby providing the support to facilitate redistribution of the fluid particles within and along the damping member 202. In other embodiments, the structural member 204 may also deform in response to the local fluid stress.

In some embodiments, the damping member 202 is defined by a single chamber (not shown) including an abating substance 210 and a plurality of baffles (not shown) that separate the chamber (not shown) into three fluidically-coupled compartments (not shown).

The damping member 202 shown in FIGS. 2A and 2B is a solid piece of material that is molded, extruded, or otherwise formed into the desired shape. The damping member 202 can be made of a biocompatible, compliant, viscoelastic material that is configured to deform in response to local fluid pressure in the artery. As the damping member 202 deforms, the damping member 202 absorbs a portion of the pulse pressure. The damping member 202, for example, can be made of a biocompatible synthetic elastomer, such as silicone rubber (VMQ), Tufel I and Tufel III elastomers (GE Advanced Materials, Pittsfield, MA), Sorbothane® (Sorbothane, Incorporated, Kent, OH), and others. The damping member 202 can be flexible and elastic such that an inner diameter of the damping member 202 increases as a systolic pressure wave propagates therethrough.

Figure 3A:
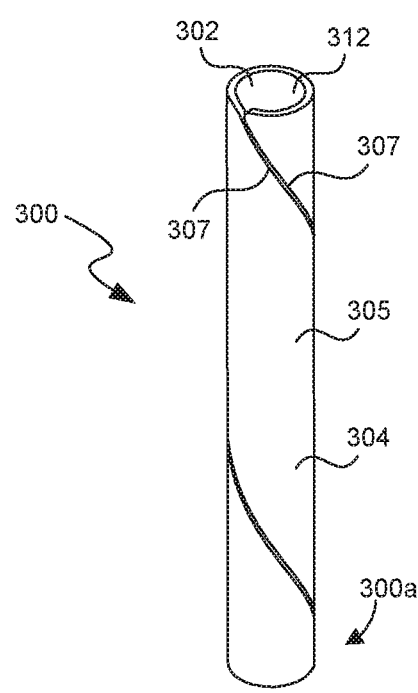
FIG. 3A is a perspective view of another embodiment of a damping device in accordance with the present technology.
Figure 3B:
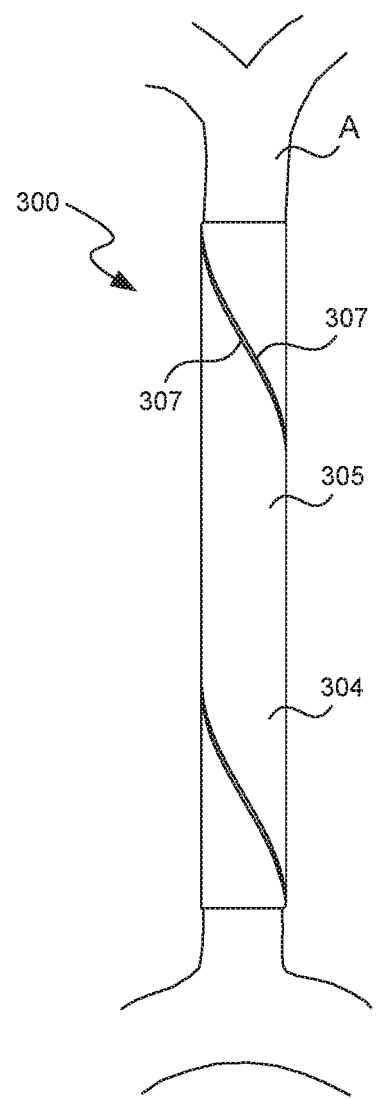
FIG. 3B is a front view of the damping device shown in FIG. 4A, shown in a deployed state positioned around a blood vessel.

FIG. 3A is a perspective view of another embodiment of a damping device 300 in accordance with the present technology, and FIG. 3B is a front view of the damping device 300, shown in a deployed state positioned around an artery A. Referring to FIGS. 3A-3B together, the damping device 300, in a deployed, relaxed state, includes a generally tubular sidewall 305 that defines a lumen. The damping device 300 can be formed of a generally parallelogram-shaped element that is wrapped around a mandrel in a helical configuration and heat set. In other embodiments, the damping device 300 can have other suitable shapes and configurations in the unfurled, non-deployed state. As shown in FIG. 3B, in the deployed state, the damping device 300 is configured to be wrapped helically along or around the circumference of an artery supplying blood to the brain. Opposing longitudinal edges 307 of the damping device 300 come together in the deployed state to form a helical path along the longitudinal axis of the artery A. The damping device 300 can include any of the coupling devices described herein to secure all or a portion of the opposing longitudinal edges to one another, such as a zip-lock type coupling mechanism, sutures, staples, adhesive, and/or other suitable coupling devices.

As best shown in FIG. 3A, the sidewall 305 of the damping device 300 includes a structural member 304 and a damping member 302. The structural member 304 can be generally similar to the structural member 204 shown in FIGS. 2A and 2B, except the structural member 304 of FIGS. 3A and 3B has a helical configuration in the deployed state. The damping member 302 can be generally similar to any of the damping members described herein, especially those described with respect to FIGS. 4A and 4B. In the embodiment shown in FIGS. 3A and 3B, the damping member 302 is positioned radially inwardly of the structural member 304 when the damping device 300 is in the deployed state. In other embodiments, the damping member 302 may be positioned radially outwardly of the structural member 304 when the damping device 300 is in the deployed state.

The damping device 300 may be configured to wrap around the circumference of the artery A so that the inner surface 312 (FIG. 3A) is adjacent and/or in contact with the outer surface of the arterial wall. In other embodiments, the damping device 300 can be configured to be positioned intravascularly (e.g., within the artery lumen) such that an outer surface of the damping device 300 is adjacent and/or in contact with the inner surface of the arterial wall. In such intravascular embodiments, the inner surface 312 of the damping member 302 is adjacent or directly in contact with blood flowing through the artery A.

Figure 4A:
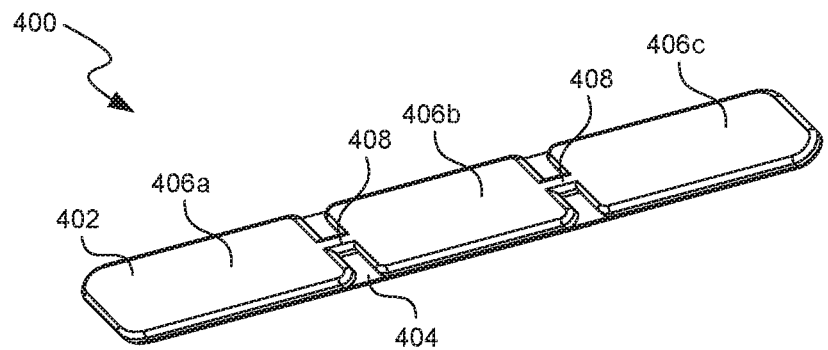
FIG. 4A is a perspective view of a damping device in accordance with another embodiment of the present technology, shown in an unwrapped state.
Figure 4B:
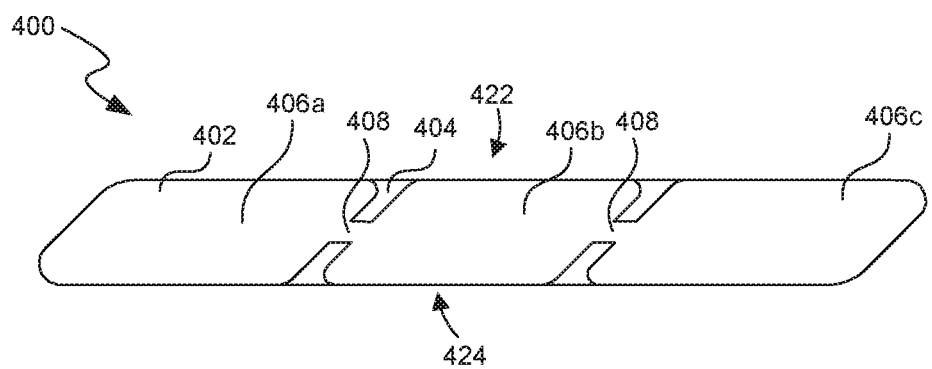
FIG. 4B is a top view of the damping device shown in FIG. 4A, shown in an unwrapped state.

FIGS. 4A and 4B are perspective and top views, respectively, of a damping device 400 that can define one embodiment of the damping device 400 shown in FIGS. 4A and 4B. In FIGS. 4A and 4B, the damping device 400 is shown in an unfurled, non-deployed state. The damping device 400 includes a damping member 402 having a plurality of chambers 406a, 406b, 406c spaced apart along a longitudinal dimension of the damping device 400 in the unfurled state. The chambers 406a, 406b, 406c may be fluidly coupled by channels 408 extending between adjacent chambers. The damping device 400 can thus operate in a manner similar to the damping device 200 where an abating substance (not shown in FIGS. 4A and 4B) in the chambers 406a-c moves through the channels 408 to inflated/deflate individual chambers in response to a pressure wave traveling through the blood vessel. The displacement of the abating substance within the chambers 406a-c attenuates the energy of the pulse wave to reduce the impact of the pulse wave distally of the damping device 400.

II. SELECTED METHODS ASSOCIATED WITH SELECTED INTRAVASCULAR EMBODIMENTS OF DAMPING DEVICES

While not illustrated in the application, the present technology also includes methods for positioning a damping device of the present disclosure at a treatment location within an artery (such as the left and/or right common carotid artery). Methods of positioning damping devices of the present disclosure include advancing a guidewire intravascularly to a treatment site from an access site, such as a femoral or a radial artery. A guide catheter may then be advanced along the guidewire until at least a distal portion of the guide catheter is positioned at the treatment site. In these and other embodiments, a rapid-exchange technique may be utilized. In some embodiments, the guide catheter may have a pre-shaped or steerable distal end portion to direct the guide catheter through one or more bends in the vasculature.

Image guidance, e.g., computed tomography (CT), fluoroscopy, angiography, intravascular ultrasound (IVUS), optical coherence tomography (OCT), or another suitable guidance modality, or combinations thereof, may be used to aid the clinician's positioning and manipulation of the damping device 200. For example, a fluoroscopy system (e.g., including a flat-panel detector, x-ray, or c-arm) can be rotated to accurately visualize and identify the target treatment site. In other embodiments, the treatment site can be determined using IVUS, OCT, and/or other suitable image mapping modalities that can correlate the target treatment site with an identifiable anatomical structure (e.g., a spinal feature) and/or a radiopaque ruler (e.g., positioned under or on the patient) before delivering damping devices of the present technology. Further, in some embodiments, image guidance components (e.g., IVUS, OCT) may be integrated with the delivery catheter and/or run in parallel with the delivery catheter to provide image guidance during positioning of damping devices of the present technology.

Once the guide catheter is positioned at the treatment site, the guidewire may be withdrawn. A delivery assembly carrying the damping device may then be advanced distally through the guide catheter to the treatment site. In some embodiments, the delivery assembly includes an elongated shaft having an atraumatic distal tip and an expandable member (e.g., an inflatable balloon, an expandable cage, etc.) positioned around a distal portion of the elongated shaft. The damping device can be positioned around the expandable member. Expansion or inflation of the expandable member forces at least a portion of the damping device radially outwardly into contact with the arterial wall. In some embodiments, the delivery assembly can include a distal expandable member for deploying a distal portion of the damping device, and a proximal expandable member for deploying a proximal portion of the damping device. In other embodiments, the entire length of the damping device may be expanded at the same time by deploying one or more expandable members.

Once the damping device is positioned at the treatment site, oxygenated blood ejected from the left ventricle flows through the lumen of the damping member. As the blood contacts the damping region of the damping member, the damping region deforms to absorb a portion of the pulsatile energy of the blood, which reduces a magnitude of a pulse pressure transmitted to the portions of the artery distal to the damping device (such as the more-sensitive cerebral arteries). The damping region acts a pressure limiter that distributes the pressure of the systolic phase of the cardiac cycle more evenly downstream from the damping device without unduly compromising the volume of blood flow through the damping device. Accordingly, the damping device reduces the pulsatile stress on downstream portions of the arterial network to prevent or at least partially reduce the manifestations of vascular dementia and/or age-related dementia.

III. SELECTED THERAPEUTIC AGENTS FOR TREATING NEUROLOGICAL CONDITIONS

In addition to providing the implantable damping device, the present technology includes providing therapeutic agents for treating neurological disorders. One of ordinary skill in the art will understand that the therapeutic agents discussed herein are illustrative of the type of therapeutic agents in the present technology, and that the present technology is not limited to the therapeutic agents explicitly discussed herein. For example, therapeutic agents not explicitly described herein but that are within the classes of therapeutic agents provided herein and/or treat the neurological conditions discussed herein are included in the present technology.

Therapeutic agents for treating neurological conditions, such as neurocognitive and/or neurodegenerative disorders, include therapeutic agents approved for use in human subjects by the Food and Drug Administration of the United States of America ("FDA"), therapeutic agents currently in clinical trials to investigate their use in human subjects such as clinical trials governed by the FDA or other similar organizations in other countries, pre-clinical therapeutic agents, and any other therapeutic agent for treating a neurological condition, or intended to treat a neurological condition. Examples of neurological conditions, such neurocognitive, neurodegenerative, or other neurological disorders include, but are not limited to, Alzheimer's disease, mild Alzheimer's disease, prodromal Alzheimer's disease, mild cognitive impairment, cerebral amyloid angiopathy, frontotemporal dementia, vascular dementia, age-related dementia, amyloidosis, Lewy body disease, Parkinson's disease, Huntington's disease, multiple sclerosis, amyotrophic lateral sclerosis, Friedreich's ataxia, and traumatic brain injury. In some embodiments, these therapeutic agents represent more than one therapeutic class of therapeutic agents, more than one mechanism of action, more than one therapeutic target, and more than one therapeutic purposes.

The therapeutic agents discussed herein have different therapeutic purposes, such as disease modifying therapeutic agents, symptomatic cognitive enhancers, and/or symptomatic agents addressing neuropsychiatric and behavioral changes. Disease modifying therapeutic agents, for example, alter the pathophysiology of the neurological condition. Symptomatic therapeutic agents, for example, mitigate and/or alleviate symptoms associated with the neurological condition. In some embodiments, a therapeutic agent is a disease modifying therapy and a symptomatic therapy. In some embodiments, a therapeutic agent may include more than one therapeutic agent.

In some embodiments, therapeutic agents of the present technology are members of general classes of therapeutic agents which include, but are not limited to, immunotherapeutic agents, small-molecule based therapeutic agents, large-molecule based therapeutic agents, DNA-based therapeutic agents, RNA-based therapeutic agents, stem-cell therapeutic agents, and natural therapeutic agents. Each of these general classes of therapeutic agents include subclasses having different mechanisms of action and therapeutic effects. As a non-limiting example, immunotherapy-based therapeutic agents may include monoclonal antibodies or antigen binding fragments thereof, polyclonal antibodies or antigen binding fragments thereof, antibody-drug conjugates, chimeric antigen receptor ("CAR") T cell therapeutic agents, T cell receptor ("TCR") therapeutic agents, and vaccines.

The therapeutic agents discussed herein have different therapeutic targets, activities, and effects. For example, therapeutic agents of the present technology include anti-amyloid therapeutic agents, anti-tau therapeutic agents, anti-inflammatory therapeutic agents, neuroprotective therapeutic agents, neurotransmitter-based therapeutic agents, metabolic therapeutic agents, antiviral therapeutic agents, and regenerative therapeutic agents. Other types of therapeutic agents include thiazolidinedione agents, neurotransmitter modulating agents, mitochondrial dynamics modulators, membrane contact site modifiers, enhancers of lysosomal function, enhancers of endosomal function, enhancers of trafficking, modifiers of protein folding, modifiers of protein aggregation, modifiers of protein stability, and modifiers of protein disposal. In some embodiments, therapeutic agents have more than one therapeutic effect. For example, therapeutic agents have one, two, three, four, five, or more different therapeutic effects. For example, in some embodiments, a therapeutic agent is an anti-amyloid therapy and an anti-tau therapy, or in some embodiments a therapeutic agent is an anti-amyloid therapy and anti-inflammatory therapy, or in some embodiments a therapeutic agent is an anti-amyloid therapy and a neuroprotective therapy, or in some embodiments a therapeutic agent is a neuroprotective therapy and an antiviral therapy, or any combination of the above.

In some embodiments, therapeutic agents of the present technology have different mechanisms of action. In some embodiments, a therapeutic agent is selected for administration to a subject in need thereof based on its mechanism of action. For example, some therapeutic agents for treating neurological conditions such as Alzheimer's disease prevent abnormal cleavage of amyloid precursor protein in a subject's brain. In some embodiments, therapeutic agents prevent expression and/or accumulation of amyloid β protein (Aβ) in the subject's brain. In some embodiments, therapeutic agents prevent expression and/or accumulation of tau protein in the subject's brain. In some embodiments, therapeutic agents treat Alzheimer's disease and other neurological conditions by increasing neurotransmission, decreasing inflammation, decreasing oxidative stress, decreasing ischemia, and/or decreasing insulin resistance.

Any of the therapeutic agents described herein, as well as other therapeutic agents which are members of the general classes of therapeutic agents described herein, are administered to the subject in need thereof at a therapeutically effective dose. Without intending to be bound by any particular dose, a therapeutically effective dose is an amount of the therapeutic agent that, when administered to the subject in need thereof, treats or at least partially treats, reduces the effects of, or at least partially reduces the effects of, the subject's condition (e.g., neurodegenerative condition). The therapeutically effective dose for each therapeutic agent is selected based upon a variety of factors, including but not limited to, one or more characteristics of the therapeutic agent (e.g., bioactivity, pharmacokinetics, pharmacodynamics, and bioavailability), the physiological condition of the subject (e.g., age, sex, disease type and stage, general physical condition, responsiveness to a given dosage, and type of medication), and the route of administration.

A. Anti-Amyloid Therapeutic Agents

In certain neurological conditions, Aβ peptides aggregate to form misfolded oligomers and amyloid plaques. For example, in Alzheimer's disease, various isoforms of Aβ (e.g., Aβ42 or Aβ40) aggregate into pathological structures, such as dimers and/or β-pleated sheet fibrils and occur following increased Aβ production, increased Aβ in the subject's plasma, increased Aβ in the subject's brain, and/or decreased Aβ clearance, among other factors. Anti-amyloid therapeutic agents include therapeutic agents that block, reduce, remove, and/or eliminate Aβ production and/or aggregation in the subject. Anti-amyloid therapeutic agents include, but are not limited to, Beta-site Amyloid precursor protein Cleavage (BACE) inhibitors, anti-amyloid immunotherapeutic agents, and anti-aggregation agents.

i. BACE Inhibitors

BACE inhibitors inhibit the function of BACE, a β-secretase enzyme that cleaves the amyloid precursor protein (APP) causing release of the C99 fragment. When the C99 fragment is released, γ-secretas, cleaves C99 to form various species of Aβ protein. Blocking BACE with a BACE inhibitor prevents and/or reduces production and/or accumulation of Aβ protein by preventing cleavage of the APP. A non-exhaustive list of BACE inhibitors includes atabecestat (JNJ-54861911, Janssen), BI 1181181 (Boehringer Ingelheim), CNP520 (Novartis), CTS-21166 (CoMentis), elenbecestat (E2609, Eisai/Biogen), HPP854 (High Point), LY2886721 (Eli Lilly), LY3202626 (Eli Lilly), lanabecestat (AZD3293, AstraZeneca), PF-05297909 (Pfizer), PF-06751979 (Pfizer), RG7129 (Roche), and verubecestat (MK-8931, Merck).

While BACE inhibitors can be administered at any therapeutically effective dose that is effective to treat the subject in need thereof, doses range from about 0.0001 to 500 mg/kg of the subject's body weight. For example, suitable dosages of BACE inhibitors are between about 0.01 mg/kg and about 500 mg/kg, between about 0.1 mg/kg and about 250 mg/kg, between about 0.1 mg/kg and about 100 mg/kg, between about 0.1 mg/kg and about 50 mg/kg, or between about 0.1 mg/kg and about 25 mg/kg. For example, a suitable dosage is one or more doses of about 0.1 mg/kg, about 0.2 mg/kg, about 0.3 mg/kg, about 0.4 mg/kg, about 0.5 mg/kg, about 1.0 mg/kg, about 1.5 mg/kg, about 2.0 mg/kg, about 3.0 mg/kg, about 4.0 mg/kg, about 5.0 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg, about 90/mg/kg, about 100 mg/kg, about 200 mg/kg, about 300 mg/kg, about 400 mg/kg, or about 500 mg/kg (or any combination thereof) of the BACE inhibitor. In some embodiments, a BACE inhibitor is administered at a flat dose, for example, about 1 mg, about 5 mg, about 10 mg, about 25 mg, about 50 mg, about 100 mg, about 200 mg, about 300 mg, about 500 mg, about 1000 mg, about 5000 mg or higher. In some embodiments, the BACE inhibitor is administered in one to fifty doses (e.g., the therapy may be delivered in a single dose, in two doses, in three doses, in four doses, in five doses, etc.). In some embodiments, the BACE inhibitor is administered chronically. In some embodiments, dosages of BACE inhibitors are administered in one or more separate administrations or by continuous infusion.

ii. Anti-Amyloid Immunotherapeutic Agents

Anti-amyloid immunotherapeutic agents target and clear aggregation of unwanted Aβ protein. For example, anti-amyloid immunotherapeutic agents reduce aggregation of Aβ proteins and/or prevent further Aβ aggregation. Anti-amyloid immunotherapeutic agents include, for example, antibodies or antigen binding fragments thereof, such as murine, chimeric (e.g., including portions derived from any other species besides a human and also from a human), humanized, or fully human antibodies, that bind to Aβ, such as monomeric, oligomeric, and/or fibril forms of Aβ. A non-exhaustive list of anti-amyloid immunotherapeutic agents includes, for example, AAB-003 (a monoclonal antibody; Janssen), ABvac 40 (an active vaccine targeting the C terminus of Aβ40; Araclon), ACI-24 (a liposome based vaccine; Janssen), AN-1792 (a synthetic Aβ peptide; Janssen), aducanumab (BIIB037; Biogen), affitope ADO2 (a synthetic Aβ fragment protein; AFFiRiS AG), BAN2401 (humanized version of mAb158, a monoclonal antibody; Biogen), bapineuzumab (AAB-001; Janssen), CAD106 (an active vaccine; Novartis), crenezumab (MABT5102A; Roche), etanercept (a TNF-α and IgG fusion protein; Amgen), GSK933776 (a monoclonal antibody; GSK), Gammagard® (pooled human plasma antibodies; Baxter), gamunex (an immunoglobulin therapy; Grifols), gantenerumab (R04909832; Roche), LY2599666 (an antigen binding fragment of a monoclonal antibody; Eli Lilly), LY3002813 (a monoclonal antibody; Eli Lilly), Lu AF20513 (an active vaccine; Otsuka), MEDI1814 (a monoclonal antibody; Eli Lilly), NPT088 (an IgG1 Fc-GAIM fusion protein; Proclara), Octagam® 10% (an intravenous immunoglobulin preparation; Octapharma), ponezumab (Pfizer), SAR228810 (a monoclonal antibody; Sanofi), solanezumab (LY20162430, Eli Lilly), UB 311 (a synthetic peptide vaccine; United Neuroscience), and vanutide cridificar (an active vaccine; ACC-001, Janssen).

While anti-amyloid therapeutic agents can be administered at any therapeutically effective dose that is effective to treat the subject in need thereof, doses range from about 0.1 mg/kg to about 250 mg/kg. For example, dosages are between about 1.0 mg/kg and about 50 mg/kg, between about 3.0 mg/kg and about 40 mg/kg, between about 5.0 mg/kg and 30 mg/kg, between about 7.0 mg/kg and about 25 mg/kg, or between about 10 mg/kg and about 20 mg/kg. For example, a dosage can also include one or more doses of about 1.0 mg/kg, about 1.5 mg/kg, about 2.0 mg/kg, about 3.0 mg/kg, about 4.0 mg/kg, about 5.0 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg, about 90/mg/kg, or about 100 mg/kg (or any combination thereof). In some embodiments, the anti-amyloid immunotherapy is administered at a flat dose of about 1 mg, about 5 mg, about 10 mg, about 25 mg, about 50 mg, about 100 mg, about 200 mg, about 300 mg, about 500 mg, about 1000 mg, or higher. For example, the anti-amyloid therapy is administered in one to fifty doses (e.g., the therapy may be delivered in a single dose, in two doses, in three doses, in four doses, in five doses, etc.). In some embodiments, the total dose administered is in the range of about 25 mg to about 5000 mg or higher, of about 50 mg to about 2500 mg, of about 50 mg to about 2000 mg, about 50 mg to about 1500 mg, about 50 mg to about 1000 mg, about 50 mg to about 500 mg, about 50 mg to about 100 mg, or any other range having a therapeutic effect on the subject's condition. For example, the total dose administered can be about 25 mg, about 50 mg, about 100 mg, about 200 mg, about 300 mg, about 400 mg, about 500 mg, about 600 mg, about 700 mg, about 1000 mg, about 1200 mg, about 1500 mg, about 1800 mg, about 2000 mg, about 2500 mg, about 3000 mg, about 4000 mg, about 5000 mg, or higher. In some embodiments, the anti-amyloid immunotherapy is administered chronically. In some embodiments, dosages of anti-amyloid therapy are administered in one or more separate administrations or by continuous infusion.

iii. Other Anti-Amyloid Aggregation Therapeutic Agents

Other anti-amyloid aggregation therapeutic agents that block, reduce, remove, and/or eliminate Aβ aggregation can be administered to the subject in need thereof to treat the condition. Other anti-amyloid aggregation therapeutic agents include, but are not limited to, vaccines, small-molecules, DNA-based therapeutic agents, RNA-based therapeutic agents, and other anti-aggregating compounds. Examples of anti-amyloid aggregation therapeutic agents include ALZT-OP1 (a cromolyn and ibuprofen combination; AZTherapies), acitretin (a retinoic acid receptor agonist; Actavis), alzhemed (a taurine variant that inhibits β-sheet formation; Neurochem), avagacestat (an arylsulfonamide γ-secretase inhibitor; Bristol-Myers Squibb), azeliragon (a RAGE inhibitor; Pfizer), bexarotene (a retinoid X receptor agonist; Ligand Pharm.), CHF 5074 (a γ-secretase modulator; CereSpir™), clioquinol (a zinc and copper chelating agent; Prana), ELND005 (neutralizes toxic, low-N Aβ oligomers; Elan), EVP-0962 (a γ-secretase modulator; Forum), elayta (CT1812, a simga2 receptor antagonist; Cognition), epigallocatechin gallate (a green tea leaf extract; Taiyo), flurizan (a selective Aβ42 lowering agent; Myriad), GV-971 (sodium oligo-mannurarate, Shanghai Green Valley Pharm.), NIC5-15 (a cyclic sugar alcohol that acts as an insulin sensitizer and modulates γ-secretase; Humanetics), insulin, PBT2 (a metal protein-attenuating compound; Prana), PF-06648671 (a γ-secretase modulator; Pfizer), PQ912 (a glutaminyl cyclase inhibitor; Probiodrug), Posiphen® (an iron regulatory protein-1 enhancer; QR Pharma), sargramostim (GM-CSF leukine, a synthetic granulocyte colony stimulator; Genzyme), semagacestat (a γ-secretase inhibitor; Eli Lilly), and thalidomide (Celgene).

While anti-amyloid therapeutic agents can be administered at any therapeutically effective dose that is effective to treat the subject in need thereof, doses range from about 0.0001 to about 500 mg/kg of body weight. For example, dosages are between about 0.1 mg/kg and about 500 mg/kg, between about 0.1 mg/kg and about 250 mg/kg, between about 0.1 mg/kg and about 100 mg/kg, between about 0.1 mg/kg and about 50 mg/kg, or between about 0.1 mg/kg and about 25 mg/kg. For example, dosages also include one or more doses of about 0.1 mg/kg, about 0.2 mg/kg, about 0.3 mg/kg, about 0.4 mg/kg, about 0.5 mg/kg, about 1.0 mg/kg, about 1.5 mg/kg, about 2.0 mg/kg, about 3.0 mg/kg, about 4.0 mg/kg, about 5.0 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg, about 90/mg/kg, about 100 mg/kg, about 200 mg/kg, about 300 mg/kg, about 400 mg/kg, or about 500 mg/kg (or any combination thereof). In some embodiments, the anti-amyloid immunotherapy is administered at a flat dose of about 1 mg, about 5 mg, about 10 mg, about 25 mg, about 50 mg, about 100 mg, about 200 mg, about 300 mg, about 500 mg, about 1000 mg, or higher. For example, the anti-amyloid therapy is administered in one to fifty doses (e.g., the therapy may be delivered in a single dose, in two doses, in three doses, in four doses, in five doses, etc.). In some embodiments, the total dose administered is in the range of about 25 mg to about 5000 mg or higher, of about 50 mg to about 2500 mg, of about 50 mg to about 2000 mg, about 50 mg to about 1500 mg, about 50 mg to about 1000 mg, about 50 mg to about 500 mg, about 50 mg to about 100 mg, or any other range having a therapeutic effect on the subject's condition. For example, the total dose administered can be about 25 mg, about 50 mg, about 100 mg, about 200 mg, about 300 mg, about 400 mg, about 500 mg, about 600 mg, about 700 mg, about 1000 mg, about 1200 mg, about 1500 mg, about 1800 mg, about 2000 mg, about 2500 mg, about 3000 mg, about 4000 mg, about 5000 mg, or higher. In some embodiments, the anti-amyloid immunotherapy is administered chronically. In some embodiments, dosages of anti-amyloid therapy are administered in one or more separate administrations or by continuous infusion.

B. Anti-Tau Therapeutic Agents

In normal physiology, tau proteins modulate the stability of axonal microtubules. In certain neurological disorders, hyperphosphorylation of tau proteins causes tangles of paired helical filaments and tau-associated neurofibrillary tangles. Anti-tau therapeutic agents, for example, block, reduce, remove, and/or eliminate production and/or aggregation of tau proteins, hyperphosphorylation of tau proteins, tangling of paired helical filaments, and/or tau-associated neurofibrillary tangles. Anti-tau therapeutic agents include, but are not limited to, vaccines, antibodies, small-molecules, DNA-based therapeutic agents, RNA-based therapeutic agents, and anti-aggregating compounds. For example, a non-exhaustive list of immunotherapeutic anti-tau therapeutic agents includes AADvac-1 (an active vaccine; Axon), ABBV-8E12 (C2N 8E12, an IgG4 monoclonal antibody; AbbVie), ACI-35 (a liposome based vaccine; AC Immune SA), BIIB076 (a monoclonal antibody; Biogen), BIIB092 (a monoclonal antibody; Biogen), JNJ-63733657 (a monoclonal antibody; Janssen), LY3303560 (a monoclonal antibody; Eli Lilly), NPT088 (an IgG1 Fc-GAIM fusion protein; Proclara), RG7345 (a monoclonal antibody; Roche), and RO 7105705 (a monoclonal antibody; Genentech). A non-exhaustive list of small-molecule and RNA-based anti-tau therapeutic agents includes ANAVEX 2-73 (a sigma-1 chaperone protein agonist; Anavex), BIIB080 (an anti-sense oligonucleotide; Biogen), epothilone D (a microtubule stabilizer; Bristol-Myers Squibb), LMTM/LMTX™ (TRx0237/methylene blue, a tau aggregation inhibitor; TauRx), nicotinamide (a histone deacetylase inhibitor), nilotinib (a tyrosine kinase inhibitor; Georgetown Univ.), TPI 287 (a tubulin-binding and microtubule-stabilizing agent; Cortice), and tideglusib (a glycogen synthase kinase 3 inhibitor; Zeltia).

While anti-tau therapeutic agents can be administered at any therapeutically effective dose that is effective to treat the subject in need thereof, doses range from about 0.0001 to about 500 mg/kg of body weight. For example, dosages are between about 0.1 mg/kg and about 500 mg/kg, between about 0.1 mg/kg and about 250 mg/kg, between about 0.1 mg/kg and about 100 mg/kg, between about 0.1 mg/kg and about 50 mg/kg, or between about 0.1 mg/kg and about 25 mg/kg. For example, dosages also include one or more doses of about 0.1 mg/kg, about 0.2 mg/kg, about 0.3 mg/kg, about 0.4 mg/kg, about 0.5 mg/kg, about 1.0 mg/kg, about 1.5 mg/kg, about 2.0 mg/kg, about 3.0 mg/kg, about 4.0 mg/kg, about 5.0 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg, about 90/mg/kg, about 100 mg/kg, about 200 mg/kg, about 300 mg/kg, about 400 mg/kg, or about 500 mg/kg (or any combination thereof). In some embodiments, the anti-tau immunotherapy is administered at a flat dose of about 1 mg, about 5 mg, about 10 mg, about 25 mg, about 50 mg, about 100 mg, about 200 mg, about 300 mg, about 500 mg, about 1000 mg, or higher. For example, the anti-tau therapy is administered in one to fifty doses (e.g., the therapy may be delivered in a single dose, in two doses, in three doses, in four doses, in five doses, etc.). In some embodiments, the total dose administered is in the range of about 25 mg to about 5000 mg or higher, of about 50 mg to about 2500 mg, of about 50 mg to about 2000 mg, about 50 mg to about 1500 mg, about 50 mg to about 1000 mg, about 50 mg to about 500 mg, about 50 mg to about 100 mg, or any other range having a therapeutic effect on the subject's condition. For example, the total dose administered can be about 25 mg, about 50 mg, about 100 mg, about 200 mg, about 300 mg, about 400 mg, about 500 mg, about 600 mg, about 700 mg, about 1000 mg, about 1200 mg, about 1500 mg, about 1800 mg, about 2000 mg, about 2500 mg, about 3000 mg, about 4000 mg, about 5000 mg, or higher. In some embodiments, the anti-tau immunotherapy is administered chronically. In some embodiments, dosages of anti-tau therapy are administered in one or more separate administrations or by continuous infusion.

C. Neurotransmitter-Based Therapeutic Agents

Neurotransmitters are endogenous molecules, amino acids, and peptides that affect neuronal signaling. Examples of neurotransmitters include glutamate, aspartate, γ-aminobutyric acid, glycine, nitric oxide, dopamine, norepinephrine, epinephrine, somatostatin, substance P, adenosine, acetylcholine, and the like.

Neurotransmitter-based therapeutic agents increase neurotransmission, the amount or activity of a neurotransmitter at a synaptic junction, in a pre-synaptic neuron, in a post-synaptic neuron, globally, or otherwise, the amount of neurotransmitter available at a synaptic junction or released in response to an electrical event by, for example, providing exogenous neurotransmitter, providing a prodrug of a neurotransmitter, increasing release of the neurotransmitter from the pre-synaptic neuron, blocking reuptake of neurotransmitters, blocking degradation of neurotransmitters, blocking or reversing inhibition of a neurotransmitter or neurotransmitter receptor, or any other mechanism designed to increase the amount or activity of neurotransmitter. In some embodiments, neurotransmitter-based therapeutic agents inhibit acetylcholinesterases and/or butyrylcholinesterases, and potentiate of nicotinic and/or muscarinic acetylcholine receptors. Other embodiments of neurotransmitter-based therapeutic agents target other neurotransmitters, enzymes, and/or receptors.

In some embodiments, neurotransmitter-based therapeutic agents decrease the amount or activity of a neurotransmitter either at a synaptic junction, in a pre-synaptic neuron, in a post-synaptic neuron, globally, or otherwise. For example, a neurotransmitter-based therapeutic agent decreases the amount of neurotransmitter available at a synaptic junction or released in response to an electrical event by blocking release of the neurotransmitter from the pre-synaptic neuron, facilitating reuptake of the neurotransmitter, enhancing degradation of the neurotransmitter, enhancing inhibition of the neurotransmitter, neutralizing the neurotransmitter, or blocking the binding-receptor of the neurotransmitter. In some embodiments, neurotransmitter-based therapeutic agents can otherwise modulate the activity or effect of a neurotransmitter.

Examples of neurotransmitter-based therapeutic agents include ABT-288 (a histamine H3 receptor antagonist; AbbVie), AVP-786 (a sigma-1 receptor agonist and a NMDA receptor antagonist; Avanir), AVP-923 (a combination of dextromethorphan and quinidine; Avanir), allopregnanolone (an allosteric modulator of GABA-a receptors), aripiprazole (a D2 receptor modulator; Bristol-Myers Squibb), atomoxetine (a norepinephrine reuptake inhibitor; Eli Lilly), AXS-05 (dextromethorphan and bupropion; Axsome), BI 409306 (a phosphodiesterase 9A inhibitor; Boehringer Ingelheim), BI 425809 (a glycine transporter I inhibitor; Boehringer Ingelheim), besipirdine HCl (a cholinergic and adrenergic neurotransmission enhancer; Aventis), bisnorcymserine (a butyrylcholinesterase inhibitor; NIA), brexpiprazole (a dopamine receptor D2 partial agonist; Otsuka), CPC-201 (a cholinesterase inhibitor and a peripheral cholinergic antagonist; Allergan), CX516 (ampalax, an ampakine; Cortex), DAOIB (a NMDA receptor modulator; Chang Gung Hospital, Taiwan), dexpramipexole (a dopamine agonist; Biogen), dimebon (Pf-01913539; Medivation), donepezil (a reversible acetylcholinesterase inhibitor), dronabinol (a CB1 and CB2 endocannabinoid receptor partial agonist; Johns Hopkins Univ.), escitalopram (a serotonin reuptake inhibitor, NIA), GSK239512 (GSK), galantamine (a cholinesterase inhibitor and an allosteric potentiator of nicotinic and muscarinic acetylcholine receptors), idalopirdine (Lu AE58054, a 5-HT6 receptor antagonist; Otsuka), intepirdine (a 5-HT6 antagonist; Axovant), lithium (an ion channel modulator), lumateperone (ITI-007, a 5-HT2a antagonist and a dopamine receptor modulator; Bristol-Myers Squibb), memantine (an NMDA antagonist), methylphenidate (a dopamine reuptake inhibitor), MK-4305 (suvorexant, a dual orexin receptor antagonist; Merck), NS2330 (a monoamine uptake inhibitor; NeuroSearch), nabilone (a cannabinoid receptor agent; Sunnybrook), neramexane (an NMDA receptor channel blocker; Forest), nicotine, ORM-12741 (an alpha-2d adrenergic receptor antagonist; Orion), octohydroaminoacridine succinate (an acetylcholinesterase inhibitor; Shanghai MHC), PF-05212377 (a 5-HT6 antagonist; Pfizer), PXT864 (a combination of baclofen and acamprosate; Pharnext), pimavanserin (a 5-HT2a inverse agonist; Acadia), piromelatine (a melatonin receptor agonist and a 5-HT-1A and 1D receptor agonist; Neurim), prazosin (an α-1 adrenergic receptor antagonist), riluzole (Sanofi), rivastigmine (an acetylcholinesterase and butyrylcholinesterase inhibitor; Novartis), rotigotine (a dopamine agonist), S 38093 (a histamine H3 receptor antagonist; Servier), S47445 (an AMPA receptor agonist; Cortex), SB 202026 (a selective muscarinic M1 receptor agonist), SGS-742 (a GABA(B) receptor antagonist; Novartis), SUVN-502 (a 5-HT6 antagonist; Suven), SUVN-G3031 (a histamine H3 receptor antagonist; Suven), sembragiline (a monoamine oxidase B inhibitor; Evotech), suritozole (a GABA-a receptor agonist; Aventis), TAK-071 (a muscarinic M1 receptor modulator; Takeda), tacrine (a reversible acetylcholinesterase inhibitor; Pfizer), valproate (a GABA transaminase inhibitor and GABA reuptake blocker; Abbott), xaliproden (a 5-HT1-A antagonist; Sanofi), and zolpidem (a positive allosteric modulator of GABA-A receptors; Brasilia Univ. Hospital).

While neurotransmitter therapeutic agents can be administered at any therapeutically effective dose that is effective to treat the subject in need thereof, doses range from about 0.0001 to about 500 mg/kg of body weight. For example, dosages are between about 0.1 mg/kg and about 500 mg/kg, between about 0.1 mg/kg and about 250 mg/kg, between about 0.1 mg/kg and about 100 mg/kg, between about 0.1 mg/kg and about 50 mg/kg, or between about 0.1 mg/kg and about 25 mg/kg. For example, dosages also include one or more doses of about 0.1 mg/kg, about 0.2 mg/kg, about 0.3 mg/kg, about 0.4 mg/kg, about 0.5 mg/kg, about 1.0 mg/kg, about 1.5 mg/kg, about 2.0 mg/kg, about 3.0 mg/kg, about 4.0 mg/kg, about 5.0 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg, about 90/mg/kg, about 100 mg/kg, about 200 mg/kg, about 300 mg/kg, about 400 mg/kg, or about 500 mg/kg (or any combination thereof). In some embodiments, the neurotransmitter immunotherapy is administered at a flat dose of about 1 mg, about 5 mg, about 10 mg, about 25 mg, about 50 mg, about 100 mg, about 200 mg, about 300 mg, about 500 mg, about 1000 mg, or higher. For example, the neurotransmitter therapy is administered in one to fifty doses (e.g., the therapy may be delivered in a single dose, in two doses, in three doses, in four doses, in five doses, etc.). In some embodiments, the total dose administered is in the range of about 25 mg to about 5000 mg or higher, of about 50 mg to about 2500 mg, of about 50 mg to about 2000 mg, about 50 mg to about 1500 mg, about 50 mg to about 1000 mg, about 50 mg to about 500 mg, about 50 mg to about 100 mg, or any other range having a therapeutic effect on the subject's condition. For example, the total dose administered can be about 25 mg, about 50 mg, about 100 mg, about 200 mg, about 300 mg, about 400 mg, about 500 mg, about 600 mg, about 700 mg, about 1000 mg, about 1200 mg, about 1500 mg, about 1800 mg, about 2000 mg, about 2500 mg, about 3000 mg, about 4000 mg, about 5000 mg, or higher. In some embodiments, the neurotransmitter immunotherapy is administered chronically. In some embodiments, dosages of neurotransmitter therapy are administered in one or more separate administrations or by continuous infusion.

D. Anti-Inflammatory Therapeutic Agents

In certain neurological disorders, such as Alzheimer's disease, microglia are overactive and increase their production of pro-inflammatory molecules such as cytokines, leading to chronic neuroinflammation. Accordingly, other categories of therapeutic agents include anti-inflammatory therapeutic agents. Anti-inflammatory therapeutic agents reduce or otherwise modulate inflammation, oxidative stress, and/or ischemia associated with neurological conditions. In some embodiments, the present technology includes anti-inflammatory therapeutic agents.

Anti-inflammatory therapeutic agents include mast cell stabilizers, such as cromolyn, a cromolyn derivative, a cromolyn analog, eugenol, nedocromil, pemirolast, olopatadine, aflatoxin, deoxynivalenol, zearalenone, ochratoxin A, fumonisin B1, hydrolyzed fumonisin B1, patulin, or ergotamine. Another useful class of anti-inflammatory therapeutic agents may include non-steroidal anti-inflammatory drugs (NSAID). NSAIDs include salicylates, propionic acid derivatives, acetic acid derivatives, enolic acid derivatives, anthranilic acid derivatives, selective COX-2 inhibitors, sulfonanilides, and others. For example, NSAIDs include acetylsalicylic acid, diflunisal, salsalate, ibuprofen, dexibuprofen, naproxen, fenoprofen, ketoprofen, dexketoprofen, flurbiprofen, oxaprozin, loxoprofen, indomethacin, tolmetin, sulindac, etodolac, ketorolac, diclofenac, nabumetone, piroxicam, meloxicam, tenoxicam, droxicam, lornoxicam, isoxicam, mefenamic acid, meclofenamic acid, flufenamic acid, tolfenamic acid, celecoxib, licofelone, hyperforin, or figwort. Further examples of anti-inflammatory therapeutic agents include ALZT-OP1 (a cromolyn and ibuprofen combination; AZTherapies), azeliragon (TTP488, a RAGE antagonist; Pfizer), CHF 5074 (an NSAID that is also a γ-secretase modulator; CereSpir), celecoxib (a selective COX-2 inhibitor; Pfizer), epigallocatechin gallate (a green tea leaf extract; Taiyo), etanercept (a TNF-α inhibitor; Pfizer), GC 021109 (a microglial activity modulator; GliaCure), GRF6019 (a plasma derived therapy; Alkahest), Gammagard® (Baxter), gamunex (an immunoglobulin preparation; Grifols), HF0220 (a glucocorticoid receptor antagonist; Newron), montelukast (a leukotriene receptor antagonist; IntelGenx), minocycline, neflamapimod (a p38 MAPKα inhibitor; EIP), NP001 (an immune regulator of inflammatory monocytes/macrophages; Neuraltus), Octagam®10% (Octapharma), PQ912 (a glutaminyl cyclase inhibitor; Probiodrug), prednisone (a corticosteroid), rofecoxib (a selective COX-2 inhibitor; Merck), and thalidomide (Celgene).

While anti-inflammatory therapeutic agents can be administered at any therapeutically effective dose that is effective to treat the subject in need thereof, doses range from about 0.0001 to about 500 mg/kg of body weight. For example, dosages are between about 0.1 mg/kg and about 500 mg/kg, between about 0.1 mg/kg and about 250 mg/kg, between about 0.1 mg/kg and about 100 mg/kg, between about 0.1 mg/kg and about 50 mg/kg, or between about 0.1 mg/kg and about 25 mg/kg. For example, dosages also include one or more doses of about 0.1 mg/kg, about 0.2 mg/kg, about 0.3 mg/kg, about 0.4 mg/kg, about 0.5 mg/kg, about 1.0 mg/kg, about 1.5 mg/kg, about 2.0 mg/kg, about 3.0 mg/kg, about 4.0 mg/kg, about 5.0 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg, about 90 mg/kg, about 100 mg/kg, about 200 mg/kg, about 300 mg/kg, about 400 mg/kg, or about 500 mg/kg (or any combination thereof). In some embodiments, the anti-inflammatory immunotherapy is administered at a flat dose of about 1 mg, about 5 mg, about 10 mg, about 25 mg, about 50 mg, about 100 mg, about 200 mg, about 300 mg, about 500 mg, about 1000 mg, or higher. For example, the anti-inflammatory therapy is administered in one to fifty doses (e.g., the therapy may be delivered in a single dose, in two doses, in three doses, in four doses, in five doses, etc.). In some embodiments, the total dose administered is in the range of about 25 mg to about 5000 mg or higher, of about 50 mg to about 2500 mg, of about 50 mg to about 2000 mg, about 50 mg to about 1500 mg, about 50 mg to about 1000 mg, about 50 mg to about 500 mg, about 50 mg to about 100 mg, or any other range having a therapeutic effect on the subject's condition. For example, the total dose administered can be about 25 mg, about 50 mg, about 100 mg, about 200 mg, about 300 mg, about 400 mg, about 500 mg, about 600 mg, about 700 mg, about 1000 mg, about 1200 mg, about 1500 mg, about 1800 mg, about 2000 mg, about 2500 mg, about 3000 mg, about 4000 mg, about 5000 mg, or higher. In some embodiments, the anti-inflammatory immunotherapy is administered chronically. In some embodiments, dosages of anti-inflammatory therapy are administered in one or more separate administrations or by continuous infusion.

E. Neuroprotective Therapeutic Agents

Neuroprotective therapeutic agents protect neurons and/or other cells or systems of the nervous system from disease pathology by decreasing cortisol production, decreasing neurodegeneration, enhancing cellular signaling and processes, enhancing mitochondrial activity, improving neurogenesis and neuroplasticity, improving neuropsychiatric symptoms, improving synaptic function, improving vascular function, protecting cellular processes, inhibiting glutamate transmission and reducing glutamate excitotoxicity, protecting against infection and inflammation, reducing cholesterol synthesis, reducing oxidative stress, reducing reactive oxygen species, regulating cAMP, stabilizing protein misfolding, and stimulating the immune system. Neuroprotective therapeutic agents include, but are not limited to, amino acids, antiviral agents, angiotensin receptor blockers, apolipoprotein E activators, effectors of cAMP activity, estrogen receptor B agonists, glucagon-like peptide 1 receptor agonists, glutamate receptor antagonists, glutamate release inhibitors, granulocyte colony stimulators, histone deacetylase inhibitors, HMG-CoA reductase inhibitors, iron chelating agents, mitochondrial function enhancing agents, monoamine oxidase B inhibitors, non-statin cholesterol reducing agents, p75 neurotrophin receptor ligands, phosphatidylinositol 3-kinase/Akt pathway activators, phosphodiesterase 3 antagonists, phosphodiesterase inhibitors, PPAR-gamma agonists, 5-hydroxytryptamine-6 receptor antagonists, and the like. Examples of neuroprotective therapeutic agents include icosapent ethyl (a purified form of the omega-3 fatty acid EPA), candesartan (an angiotensin receptor blocker), cilostazol (a phosphodiesterase 3 antagonist; Otsuka), deferiprone (an iron chelating agent), DHP1401 (a cAMP activity effector; Daehwa), ID1201 (a phosphatidylinositol 3-kinase/Akt pathway activator; IlDong), liraglutide (a glucagon-like peptide 1 receptor agonist; Novo Nordisk), LM11A-31-BHS (a p75 neurotrophin receptor ligand; PharmatrophiX), L-serine, MLC901 (NeuroAiD™ II, a natural herbal medicine), MP-101 (a mitochondrial function enhancer; Mediti), nicotinamide (a histone deacetylase inhibitor), probucol (a non-statin cholesterol reducing agent), rasagiline (a monoamine oxidase B inhibitor; Teva), riluzole, sargramostim (a synthetic granulocyte colony stimulator), s-equol (an estrogen receptor B agonist; Ausio), SLAT (a HMG-CoA reductase inhibitor and antioxidant; Merck), STA-1 (an antioxidant; Sinphar), telmisartan (an angiotensin II receptor blocker and a PPAR-gamma agonist; Boehringer Ingelheim), valacyclovir (an antiviral agent), vorinostat (a histone deacetylase inhibitor), and xanamema (a 11-HSD1 enzyme inhibitor; Actinogen).

While neuroprotective therapeutic agents can be administered at any therapeutically effective dose that is effective to treat the subject in need thereof, doses range from about 0.0001 to about 500 mg/kg of body weight. For example, dosages are between about 0.1 mg/kg and about 500 mg/kg, between about 0.1 mg/kg and about 250 mg/kg, between about 0.1 mg/kg and about 100 mg/kg, between about 0.1 mg/kg and about 50 mg/kg, or between about 0.1 mg/kg and about 25 mg/kg. For example, dosages also include one or more doses of about 0.1 mg/kg, about 0.2 mg/kg, about 0.3 mg/kg, about 0.4 mg/kg, about 0.5 mg/kg, about 1.0 mg/kg, about 1.5 mg/kg, about 2.0 mg/kg, about 3.0 mg/kg, about 4.0 mg/kg, about 5.0 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg, about 90/mg/kg, about 100 mg/kg, about 200 mg/kg, about 300 mg/kg, about 400 mg/kg, or about 500 mg/kg (or any combination thereof). In some embodiments, the neuroprotective immunotherapy is administered at a flat dose of about 1 mg, about 5 mg, about 10 mg, about 25 mg, about 50 mg, about 100 mg, about 200 mg, about 300 mg, about 500 mg, about 1000 mg, or higher. For example, the neuroprotective therapy is administered in one to fifty doses (e.g., the therapy may be delivered in a single dose, in two doses, in three doses, in four doses, in five doses, etc.). In some embodiments, the total dose administered is in the range of about 25 mg to about 5000 mg or higher, of about 50 mg to about 2500 mg, of about 50 mg to about 2000 mg, about 50 mg to about 1500 mg, about 50 mg to about 1000 mg, about 50 mg to about 500 mg, about 50 mg to about 100 mg, or any other range having a therapeutic effect on the subject's condition. For example, the total dose administered can be about 25 mg, about 50 mg, about 100 mg, about 200 mg, about 300 mg, about 400 mg, about 500 mg, about 600 mg, about 700 mg, about 1000 mg, about 1200 mg, about 1500 mg, about 1800 mg, about 2000 mg, about 2500 mg, about 3000 mg, about 4000 mg, about 5000 mg, or higher. In some embodiments, the neuroprotective immunotherapy is administered chronically. In some embodiments, dosages of neuroprotective therapy are administered in one or more separate administrations or by continuous infusion.

F. Metabolic Therapeutic Agents

Metabolic therapeutic agents, for example, reduce inflammation, reduce oxidative stress, and prevent ischemia, and as such, alter one or more cellular pathways, alter cellular plasticity, enhance cell signaling and neurogenesis, enhance mitochondrial activity, improve cellular processes, improve synaptic dysfunction, improve vascular functioning, inactivate reactive oxygen species, increase insulin signaling, reduce neuronal hyperactivity, and/or regulate cAMP function. Metabolic therapeutic agents include, but are not limited to, angiotensin receptor blockers, anticonvulsant agents, β2 adrenergic receptor agonists, GABA receptor modulators, glucagon-like peptide 1 receptor agonists, insulin based therapeutic agents, monoamine oxidase B inhibitors, protein kinase C modulators, selective p38 MAPK alpha inhibitors, sigma-2 receptor modulators, thiamine based therapeutic agents, tyrosine kinase Fyn inhibitors, phosphodiesterase 3 antagonists, phosphatidylinositol 3-kinase/Akt pathway activators, vaccines, and the like. Examples of metabolic therapeutic agents include allopregnanolone (a GABA receptor modulator), benfotiamine (synthetic thiamine), bryostatin 1 (a protein kinase C modulator; Neurotrope), cilostazol (a phosphodiesterase type 3 inhibitor), CT1812 (a sigma-2 receptor modulator; Cognition), DHP1401 (a cAMP activity effector; Daehwa), formoterol (a β2 adrenergic receptor agonist; Mylan), GV1001 (a telomerase reverse transcriptase peptide vaccine; GemVax), Humulin (a concentrated human insulin; Eli Lilly), ID1201 (a phosphatidylinositol 3-kinase/Akt pathway activator; IlDong), insulin, levetiracetam (an anticonvulsant), liraglutide (a glucagon-like peptide 1 receptor agonist), oxaloacetate (a mitochondrial enhancer), rasagiline (a monoamine oxidase inhibitor), saracatinib (AZD0530, a tyrosine kinase Fyn inhibitor; AstraZeneca), and VX-745 (neflamapimod, a selective p38 MAPK alpha inhibitor; EIP).

While metabolic therapeutic agents can be administered at any therapeutically effective dose that is effective to treat the subject in need thereof, doses range from about 0.0001 to about 500 mg/kg of body weight. For example, dosages are between about 0.1 mg/kg and about 500 mg/kg, between about 0.1 mg/kg and about 250 mg/kg, between about 0.1 mg/kg and about 100 mg/kg, between about 0.1 mg/kg and about 50 mg/kg, or between about 0.1 mg/kg and about 25 mg/kg. For example, dosages also include one or more doses of about 0.1 mg/kg, about 0.2 mg/kg, about 0.3 mg/kg, about 0.4 mg/kg, about 0.5 mg/kg, about 1.0 mg/kg, about 1.5 mg/kg, about 2.0 mg/kg, about 3.0 mg/kg, about 4.0 mg/kg, about 5.0 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg, about 90/mg/kg, about 100 mg/kg, about 200 mg/kg, about 300 mg/kg, about 400 mg/kg, or about 500 mg/kg (or any combination thereof). In some embodiments, the metabolic immunotherapy is administered at a flat dose of about 1 mg, about 5 mg, about 10 mg, about 25 mg, about 50 mg, about 100 mg, about 200 mg, about 300 mg, about 500 mg, about 1000 mg, or higher. For example, the metabolic therapy is administered in one to fifty doses (e.g., the therapy may be delivered in a single dose, in two doses, in three doses, in four doses, in five doses, etc.). In some embodiments, the total dose administered is in the range of about 25 mg to about 5000 mg or higher, of about 50 mg to about 2500 mg, of about 50 mg to about 2000 mg, about 50 mg to about 1500 mg, about 50 mg to about 1000 mg, about 50 mg to about 500 mg, about 50 mg to about 100 mg, or any other range having a therapeutic effect on the subject's condition. For example, the total dose administered can be about 25 mg, about 50 mg, about 100 mg, about 200 mg, about 300 mg, about 400 mg, about 500 mg, about 600 mg, about 700 mg, about 1000 mg, about 1200 mg, about 1500 mg, about 1800 mg, about 2000 mg, about 2500 mg, about 3000 mg, about 4000 mg, about 5000 mg, or higher. In some embodiments, the metabolic immunotherapy is administered chronically. In some embodiments, dosages of metabolic therapy are administered in one or more separate administrations or by continuous infusion.

G. Antiviral Therapeutic Agents

Antiviral therapeutic agents prevent, reduce, and/or eliminate aggregation of Aβ or tau protein and include, but are not limited to valacyclovir. Antiviral therapeutic agents are administered at a dose effective to treat the subject's neurological condition. Dosages can be administered in one or more administrations or by continuous infusion. Doses range from about 0.001 mg/kg to about 500 mg/kg or higher. In some embodiments, a flat dose may be provided, such as, for example, about 100 mg, about 200 mg, about 300 mg, about 400 mg, or about 500 mg.

H. Regenerative Therapeutic Agents

Regenerative therapeutic agents enhance neuroplasticity, promote neurogenesis, and/or regenerate neurons. In some embodiments, regenerative therapies include, but are not limited to, immunotherapies, small-molecule agents, stem cell therapies, and growth factors. Stem cell therapies include, for example, human mesenchymal stem cells. Examples of regenerative therapies include AstroStem (autologous adipose tissue derived mesenchymal stem cells; Nature Cell Co.), CB-AC-02 (placenta derived MSCs; CHA Biotech), hUCB-MSCs (stem cell therapy; Medipost), hMSCs (stem cell therapy; Longeveron), and NDX-1017 (hepatocyte growth factor; M3).

Regenerative therapeutic agents are administered at a dose effective to treat the subject's neurological condition. Dosages can be administered in one or more administrations or by continuous infusion. Doses range from about 1 million to about 250 million stem cells. In some embodiments, the dose is about 10 million to about 200 million stem cells, about 15 million to about 150 million stem cells, or about 20 million to about 100 million stem cells.

I. ADDITIONAL THERAPEUTIC AGENTS

An additional therapeutic agent for treatment of a subject's condition in accordance with the present technology is aducanumab, an anti-amyloid immunotherapy. Aducanumab is a high-affinity, fully human IgG1 monoclonal antibody that binds a conformational epitope of Aβ on both oligomeric and fibrillar forms of Aβ to prevent and/or reduce Aβ aggregation. In some embodiments, aducanumab is administered monthly and in a plurality of doses, such as between about 0.1 mg/kg and about 75 mg/kg, between about 1 mg/kg and about 60 mg/kg, between about 1 mg/kg and about 15 mg/kg, or between about 1 mg/kg and/or about 10 mg/kg. In some embodiments, aducanumab is administered at a dose of about 1 mg/kg, about 3 mg/kg, about 6 mg/kg, about 10 mg/kg, about 30 mg/kg, or about 60 mg/kg. Repetitive doses of aducanumab can be constant (e.g., monthly doses of about 3 mg/kg) or can be escalating (e.g., about 1 mg/kg for month 1, about 3 mg/kg for months 2-4, about 6 mg/kg for months 5-10, and about 10 mg/kg for months 11 and 12). In some embodiments, aducanumab is administered for a period of one year. In other embodiments, aducanumab is administered chronically.

Yet another additional therapeutic agent for treatment of a subject's condition in accordance with the present technology is BAN2401. BAN2401 is a humanized IgG1 monoclonal antibody that binds to Aβ protofibrils. Infusions or other administrations of BAN2401 can occur daily, weekly, bi-weekly, monthly, or on any other schedule designed to achieve a therapeutic effect on the subject in need thereof. In some embodiments, BAN2401 is administered bi-weekly. In some embodiments, doses of BAN2401 are selected from ranges between about 1 mg/kg to about 50 mg/kg, between about 2 mg/kg and about 25 mg/kg, and/or between about 2.5 mg/kg and about 10 mg/kg. In some embodiments, BAN2401 is administered at a dose of about 2.5 mg/kg, about 5 mg/kg, or about 10 mg/kg. In some embodiments, BAN2401 is administered for a period between about four months and about one year. In some embodiments, BAN2401 is administered chronically.

One skilled in the art will understand that the foregoing therapies and accompanying description is for illustrative purposes and does not limit the therapies that may be provided in certain embodiments of the present technology. Accordingly, any therapy useful in or designed to treat a neurological condition, such as a neurodegenerative condition, may be present in certain embodiments of the present technology.

IV. SELECTED METHODS OF TREATING NEUROLOGICAL CONDITIONS WITH A COMBINATION OF AN IMPLANTABLE DAMPING DEVICE AND A THERAPEUTIC AGENT

Reducing a subject's pulse pressure with the implantable damping devices has subsequent downstream impacts on other factors that contribute to onset, duration, and/or progression of the subject's condition (e.g., neurological condition), such as, but not limited to, increased expression of sRAGE, decreased levels of plasma and brain amyloid β, and decreased levels of tau protein. These factors, in addition to others, contribute to inflammation, oxidative stress, ischemia, and insulin resistance which subsequently cause synaptic and/or neuronal dysfunction and impaired neurotransmission. This occurs in subjects suffering from conditions such as progressive cognitive dysfunction and dementia.

Several biological pathways, for example such as those described herein, may contribute to a neurological condition (e.g., dementia). Without intending to be bound by any particular theory, it is thought that interfering (e.g., altering, effecting, impairing, inhibiting, reducing, or otherwise changing the function of) two or more biological pathways is more effective for treating, preventing, or otherwise reducing the subject's neurological condition, and/or symptoms thereof, rather than interfering with a single biological pathway. In this way, the effects of combining the implantable damping device and at least one therapeutic agent of the present technology may be complementary, additive or even synergistic when compared to an effect of the implantable damping device and the therapeutic agent alone. Accordingly, combining the implantable damping devices with one or more therapeutic agents that affect these other factors further treats and/or slows one or more effects of the condition.

As described above, combinatorial therapies of the present technology include an implantable damping device and a therapeutic agent (e.g., a drug) for treating or slowing the progression of the condition. Some embodiments of the present technology, for example, are directed to combinatorial therapies including the implantable damping devices described above under Headings I-III and one or more therapeutic agents that target these factors. Some of these therapeutic agents are described above under Heading IV and include, but are not limited to, BACE-inhibitors, anti-amyloid immunotherapies, anti-amyloid aggregation therapies, anti-tau therapies, neurotransmitter based therapies, neuroprotective and/or anti-inflammatory therapies, metabolic therapies, and antiviral therapies. When combined, the implantable damping devices and therapeutic agents of the present technology have a greater effect on treating or slowing one or more effects of the condition upon a subject when compared either to the effects of the implantable damping device or therapeutic agent alone. For example, providing an implantable damping device that reduces the subject's pulse pressure and an anti-amyloid therapy that reduces formation of amyloid in the subject's brain and blood vessel walls improves synaptic and/or neuronal function and neurotransmission, thereby treating or slowing progressive cognitive dysfunction and dementia.

Figure 5:
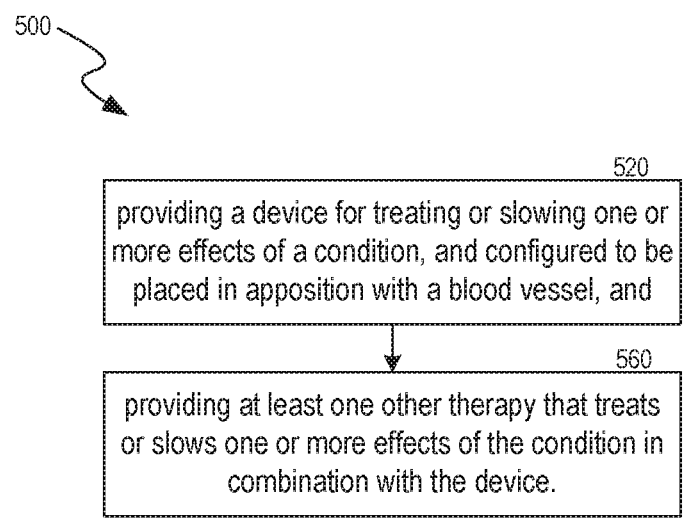
FIG. 5 is a flow chart illustrating a method in accordance with the present technology.

FIG. 5 is a flow chart illustrating method 500 for treating or slowing one or more effects of a subject's condition. At block 520, the method 500 provides a device for treating or slowing one or more effects of the condition. The device is the implantable damping devices of the present technology and is configured to be placed in apposition with the subject's blood vessel. Similar to other devices of the present technology, the device provided in method 500 includes the flexible damping member having both the inner surface formed of the sidewall having one or more at least partially deformable portions and the outer surface. In addition, the abating substance is disposed within the partially deformable portions and is configured to move longitudinally and/or radially therein in response to pulsatile blood flow within the blood vessel. At block 560, the method 500 provides at least one other therapy that treats or slows one or more effects of the condition in combination with the implantable damping device. In some embodiments, the other therapy is provided to the subject before the implantable damping device, up to about 24 hours, up to about 7 days, up to about 4 weeks, up to about 12 months, or up to about 5 years before the implantable damping device. In other embodiments, the implantable damping device is provided to the subject before the other therapy, up to about 24 hours, up to about 7 days, up to about 4 weeks, up to about 12 months, or up to about 5 years before the other therapy. For example, the other therapy (e.g., therapeutic agent) or the implantable damping device is provided to the subject about 0 to about 24 hours, about 1 to about 5 hours, about 3 to about 12 hours, about 5 to about 10 hours, about 1 day to about 7 days, about 2 days to about 6 days, about 3 days to about 5 days, about 1 week to about 4 weeks, about 2 weeks to about 4 weeks, about 1 week to about 3 weeks, about 2 weeks to about 3 weeks, about 1 year to about 5 years, about 1 year to about 4 years, about 2 years to about 5 years, about 2 years to about 4 years, about 3 years to about 4 years, or about 4 years to about 5 years before the implantable damping device or the other therapy (e.g., therapeutic agent), respectively.

As described above under heading III, the at least one other therapy of the methods of the present technology is provided to the subject by administration. In some embodiments, the other therapy (e.g., therapeutic agent) is selected from the group consisting of a BACE inhibitor, a tau inhibitor, an amyloid immunotherapeutic agent, an amyloid aggregation inhibitor, an anti-inflammatory agent, a neuroprotective agent, an antiviral agent, a metabolic agent, a thiazolidinedione agent, a neurotransmitter agent, a mitochondrial dynamics modulator, a membrane contact site modifier, an enhancer of lysosomal function, an enhancer of endosomal function, an enhancer of trafficking, a modifier of protein folding, a modifier of protein aggregation, a modifier of protein stability, and a modifier of protein disposal. In some embodiments, the amyloid immunotherapeutic agent is an anti-amyloid antibody. The anti-amyloid antibody is a humanized version of mouse monoclonal antibody mAb158, e.g., an IgG1 antibody such as BAN2401, or a human anti-amyloid antibody such as aducanumab. In some embodiments, the at least one other therapy prevents abnormal cleavage of amyloid precursor protein in the subject's brain, prevents expression and/or accumulation of amyloid β protein in the subject's brain, prevents expression and/or accumulation of tau protein in the subject's brain, increases neurotransmission, decreases inflammation, decreases oxidative stress, decreases ischemia, and/or decreases insulin resistance.

When combined with the implantable damping devices of the present technology, the therapeutic agents described herein are provided at a first dosage that is lower than a second dosage of the same therapeutic agents provided in the absence of the implantable damping devices (e.g., subjects receiving only the therapeutic agents rather than in combination with the implantable damping devices). For example, a subject having a neurodegenerative condition, such as dementia, is provided with a lower dose of BAN2401 before, during, or after being provided with the implantable damping device compared to a subject provided with a dose of BAN2401 without also being provided with the implantable damping device.

In some embodiments, when combined with the implantable damping devices of the present technology, the therapeutic agents described herein are provided with a first dosing regimen which is less than a second dosing regimen of the same therapeutic agents that is provided in the absence of the implantable damping devices. For example, a subject having a neurodegenerative condition, such as dementia, is provided with a first dosing regimen of BAN2401 before, during, or after being provided with the implantable damping device compared to a subject provided with a second dosing regimen of BAN2401 without also being provided with the implantable damping device.

In some embodiments, when combined with the implantable damping devices of the present technology, the therapeutic agents described herein are provided with the therapeutic agent by a first route which differs from a second route provided in the absence of the implantable damping devices. For example, a subject having a neurodegenerative condition, such as dementia, is provided with BAN2401 by the first route before, during, or after being provided with the implantable damping device compared to a subject provided with BAN2401 by the second route without also being provided with the implantable damping device. In some embodiments, the route of administration includes delivering the therapeutic agent to the subject from the device, for example, by eluting the therapeutic agent previously stored in at least a portion of the device.

V. SELECTED SYSTEMS FOR TREATING NEUROLOGICAL CONDITIONS WITH A COMBINATION OF AN IMPLANTABLE DAMPING DEVICE AND A THERAPEUTIC AGENT

In addition to the methods, damping devices, and therapeutic agents described herein, the present technology also includes associated systems for treating or slowing one or more effects of the subject's condition. Systems of the present technology include an effective amount of at least one therapy for treating or slowing one or more effects of the condition and a device for treating or slowing one or more effects of the condition. As explained above, devices of the present technology include at least a flexible damping member forming a generally tubular structure having an inner surface formed of a sidewall having one or more at least partially deformable portions, and an abating substance disposed within and configured to move longitudinally and/or radially within one partially deformable portion in response to pulsatile blood flow within the blood vessel. In some embodiments, the therapy includes at least one or more therapeutic agents that may be carried by the damping device. In these embodiments, the therapeutic agent is disposed within and/or carried by at least one or more of the at least partially deformable portions of the damping device. When one or more of the at least partially deformable portions of the damping device are at least partially deformed, the effective amount of the therapeutic agent may be released from the device.

VI. EXAMPLES

The following examples are illustrative of several embodiments of the present technology.

A. Example 1

Implantable devices will be positioned at, near, around, within, or in place of at least a portion of a subject's artery in accordance with the present technology. After the implantable devices have been positioned, subjects who received the implantable device will be randomized into at one of at least two groups: Group A—placebo, and Group B—drug. The placebo will be an experimentally appropriate placebo useful for distinguishing any specific effects of the drug, such as the pharmaceutically acceptable carrier for the active pharmaceutical ingredient ("API") in the drug. The dose of the placebo will be comparable to the amount of pharmaceutically acceptable carrier that subjects in Group B receive. Group B can include two or more subgroups, with subjects being randomly assigned to each subgroup. While the subjects in each of these Group B subgroups each ultimately receive the same drug, the dose, route of administration, dosing regimen, or other parameters associated with a therapeutic protocol can be altered.

B. Example 2

A drug will be delivered to a subject at a pre-specified dose, route of administration, frequency, and duration. After the drug has been delivered to the subject, subjects will be randomized into at one of at least two groups: Group A—sham, and Group B—implantable device. For those subjects in Group B, implantable devices will be positioned at, near, around, within, or in place of at least a portion of a subject's artery in accordance with the present technology. The sham treatment for Group A includes the delivery methods associated with delivery of the implantable device used for Group B, although the implantable device will not be delivered to the subjects in Group A.

VII. CONCLUSION

Although many of the embodiments are described above with respect to systems, devices, and methods for treating and/or slowing the progression of vascular and/or age-related neurological conditions (e.g., dementia) via combinatorial therapeutic agents (e.g., drugs) and intravascular methods, the technology is applicable to other applications and/or other approaches, such as surgical implantation of one or more damping devices and/or treatment of blood vessels other than arterial blood vessels supplying blood to the brain, such as the abdominal aorta, in combination with one or more drugs. Any appropriate site within a blood vessel may be treated including, for example, the ascending aorta, the aortic arch, the brachiocephalic artery, the right subclavian artery, the left subclavian artery, the left common carotid artery, the right common carotid artery, the internal and external carotid arteries, and/or branches of any of the foregoing. Moreover, other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described above with reference to FIGS. 2A-5.

The above detailed descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A system for use in treating or slowing one or more effects of a condition in a subject in need thereof, the system comprising:
   an effective amount of at least one therapy for treating or slowing one or more effects of the condition, and
   a device for treating or slowing one or more effects of the condition,
   the device comprising—
   a flexible damping member forming a generally tubular structure having an inner surface and an outer surface, the inner surface formed of a sidewall having one or more at least partially deformable portions configured to move longitudinally and/or radially within the one or more at least partially deformable portions in response to pulsatile blood flow within the blood vessel;
   wherein, the effective amount of the at least one therapy for treating or slowing one or more effects of the condition is carried by at least one or more of the at least partially deformable portions of the device, and
   wherein, when the one or more at least partially deformable portions are at least partially deformed, the effective amount of at least one therapy for treating or slowing one or more effects of the condition is released from the device.

2. The system of claim 1, wherein the effective amount of the at least one therapy further comprises a first effective amount of the at least one therapy and a second effective amount of the at least one therapy.

3. The system of claim 2, wherein a) the second effective amount of the at least one therapy is greater than the first effective amount of the at least one therapy; or
   b) the second effective amount of the at least one therapy is greater than the first effective amount of the at least one therapy and wherein, in response to a first pulsatile blood flow within the blood vessel, the one or more at least partially deformable portions are at least partially deformed to (a) a first degree of deformation, (b) a second degree of deformation, or both (a) and (b); or
   c) the second effective amount of the at least one therapy is greater than the first effective amount of the at least one therapy and wherein, in response to a first pulsatile blood flow within the blood vessel, the one or more at least partially deformable portions are at least partially deformed to (a) a first degree of deformation, (b) a second degree of deformation, or both (a) and (b) and wherein the second degree of deformation is greater than the first degree of deformation; or
   d) the second effective amount of the at least one therapy is greater than the first effective amount of the at least one therapy and wherein, in response to a first pulsatile blood flow within the blood vessel, the one or more at least partially deformable portions are at least partially deformed to (a) a first degree of deformation, (b) a second degree of deformation, or both (a) and (b) and wherein the second degree of deformation is greater than the first degree of deformation and wherein (a) the first effective amount of the at least one therapy is released from the one or more at least partially deformable portions in response to the first degree of deformation; (b) the second effective amount of the at least one therapy is released from the one or more at least partially deformable portions in response to the second degree of deformation; or (c) both (a) and (b).

4. The system of claim 1, wherein the at least one therapy is selected from the group consisting of a β-site amyloid precursor protein cleaving enzyme (BACE) inhibitor, a tau inhibitor, an amyloid immunotherapeutic agent, an amyloid aggregation inhibitor, an anti-inflammatory agent, a neuroprotective agent, an antiviral agent, a metabolic agent, a thiazolidinedione agent, a neurotransmitter agent, a mitochondrial dynamics modulator, a membrane contact site modifier, an enhancer of lysosomal function, an enhancer of endosomal function, an enhancer of trafficking, a modifier of protein folding, a modifier of protein aggregation, a modifier of protein stability, and a modifier of protein disposal.

5. The system of claim 4, wherein the amyloid immunotherapeutic agent is an anti-amyloid antibody, preferably aducanumab.

6. The system of claim 1, wherein the at least one therapy is used to prevent abnormal cleavage of amyloid precursor protein in the subject's brain, prevent expression and/or accumulation of amyloid ß protein in the subject's brain, prevent expression and/or accumulation of tau protein in the subject's brain, increase neurotransmission, decrease inflammation, decrease oxidative stress, decrease ischemia, and/or decrease insulin resistance.

7. The system of claim 1, wherein the at least one therapy is provided at a first dosage or dosing regimen which is lower or less than a second dosage or dosing regimen that is provided in the absence of the device.

8. The system claim 1, wherein the at least one therapy is provided via a first route which is different than a second route that is provided in the absence of the device.

9. The system of claim 1, wherein the condition is neurodegeneration.

10. The system of claim 9, wherein neurodegeneration further comprises Alzheimer's disease, dementia, and/or cognitive impairment.

11. The system of claim 1, wherein the inner surface and/or an outer surface has a generally cylindrical shape or an undulating shape that undulates in a longitudinal direction.

12. The system of claim 1, wherein the device has a low-profile state and a deployed state, and when in the deployed state, the sidewall is generally tubular.

13. The system of claim 12, wherein when positioned in apposition with the blood vessel and a pulse wave travels through the blood vessel, the flexible damping member applies a stress at the first location along a length of the tubular structure.

14. The system of claim 1, wherein the flexible damping member is further configured to be positioned around at least a portion of a circumference of a wall of the blood vessel and a pulse wave traveling through the blood vessel applies a stress at a first region of the damping member, such that the damping member absorbs at least a portion of the energy of the pulse wave, thereby reducing the stress on the blood vessel wall distal to the device.

15. The system of claim 1, wherein the device is further configured to be deployed within a lumen of the blood vessel such that an outer surface of an anchoring member is in apposition with a lumen of the blood vessel wall and the outer surface of the sidewall is in contact with blood flowing through the blood vessel lumen.

* * * * *